(12) United States Patent
Gormley et al.

(10) Patent No.: US 9,574,226 B2
(45) Date of Patent: Feb. 21, 2017

(54) METHODS OF NUCLEIC ACID SEQUENCING

(71) Applicant: ILLUMINA CAMBRIDGE LIMITED, Little Chesterford Nr, Saffron Walden Essex (GB)

(72) Inventors: Niall Anthony Gormley, Cambridge (GB); Louise Fraser, Cambridge (GB); Paula Kokko-Gonzales, Cambridge (GB)

(73) Assignee: Illumina, Inc., San Diego, CA (US)

( * ) Notice: Subject to any disclaimer, the term of this patent is extended or adjusted under 35 U.S.C. 154(b) by 94 days.

(21) Appl. No.: 14/378,613

(22) PCT Filed: Mar. 6, 2013

(86) PCT No.: PCT/EP2013/054517
§ 371 (c)(1),
(2) Date: Aug. 13, 2014

(87) PCT Pub. No.: WO2013/131962
PCT Pub. Date: Sep. 12, 2013

(65) Prior Publication Data
US 2015/0087534 A1    Mar. 26, 2015

Related U.S. Application Data

(60) Provisional application No. 61/607,418, filed on Mar. 6, 2012.

(51) Int. Cl.
*C12Q 1/68* (2006.01)

(52) U.S. Cl.
CPC ........... *C12Q 1/6806* (2013.01); *C12Q 1/6834* (2013.01); *C12Q 1/6869* (2013.01)

(58) Field of Classification Search
CPC ... C12Q 1/6806; C12Q 1/6869; C12Q 1/6834; C12Q 1/6837; C12Q 2565/518; C12Q 2521/107
See application file for complete search history.

(56) References Cited

U.S. PATENT DOCUMENTS

| | | | | |
|---|---|---|---|---|
| 9,029,103 B2 * | 5/2015 | Rigatti | ................. | C12Q 1/6874 435/6.1 |
| 2006/0121461 A1 * | 6/2006 | Harms | ............... | C12N 15/1034 435/6.14 |
| 2012/0053063 A1 * | 3/2012 | Rigatti | ................. | C12Q 1/6874 506/2 |
| 2015/0225787 A1 * | 8/2015 | Rigatti | ................. | C12Q 1/6874 506/3 |
| 2016/0090591 A1 * | 3/2016 | Goryshin | ........... | C12N 15/1065 506/16 |

FOREIGN PATENT DOCUMENTS

| | | | | |
|---|---|---|---|---|
| CA | 2803693 | 3/2012 | | |
| CN | 102264914 | 11/2011 | | |
| WO | WO 2010048605 A1 * | 4/2010 | ........... | C12N 9/1252 |
| WO | WO 2012106546 A2 * | 8/2012 | ......... | C12N 15/1093 |
| WO | WO 2012135664 A2 * | 10/2012 | ............. | C12Q 1/686 |

OTHER PUBLICATIONS

Caruccio et al., "Preparation of next-generation sequencing libraries using Nextera™ technology: simultaneous DNA fragmentation and adaptor tagging by in vitro transpoition", Methods in Molecular Biology, vol. 733, 241-255 (2011).

\* cited by examiner

*Primary Examiner* — Jennifer Dunston
(74) *Attorney, Agent, or Firm* — Fletcher Yoder, P.C.

(57) ABSTRACT

Provided herein is a method of using transposition to improve methods of sequencing RNA molecules. Provided herein is a method of tagging nucleic acid duplexes, such as DNA:RNA duplexes or DNA:DNA duplexes. The method includes the steps of providing a transposase and a transposon composition, providing one or more nucleic acid duplexes immobilized on a support, and contacting the transposase and transposon composition with the one or more nucleic acid duplexes under conditions wherein the one or more nucleic acid duplexes and transposon composition undergo a transposition reaction to produce one or more tagged nucleic acid duplexes, wherein the transposon composition comprises a double stranded nucleic acid molecule comprising a transferred strand and a non-transferred strand.

35 Claims, 11 Drawing Sheets

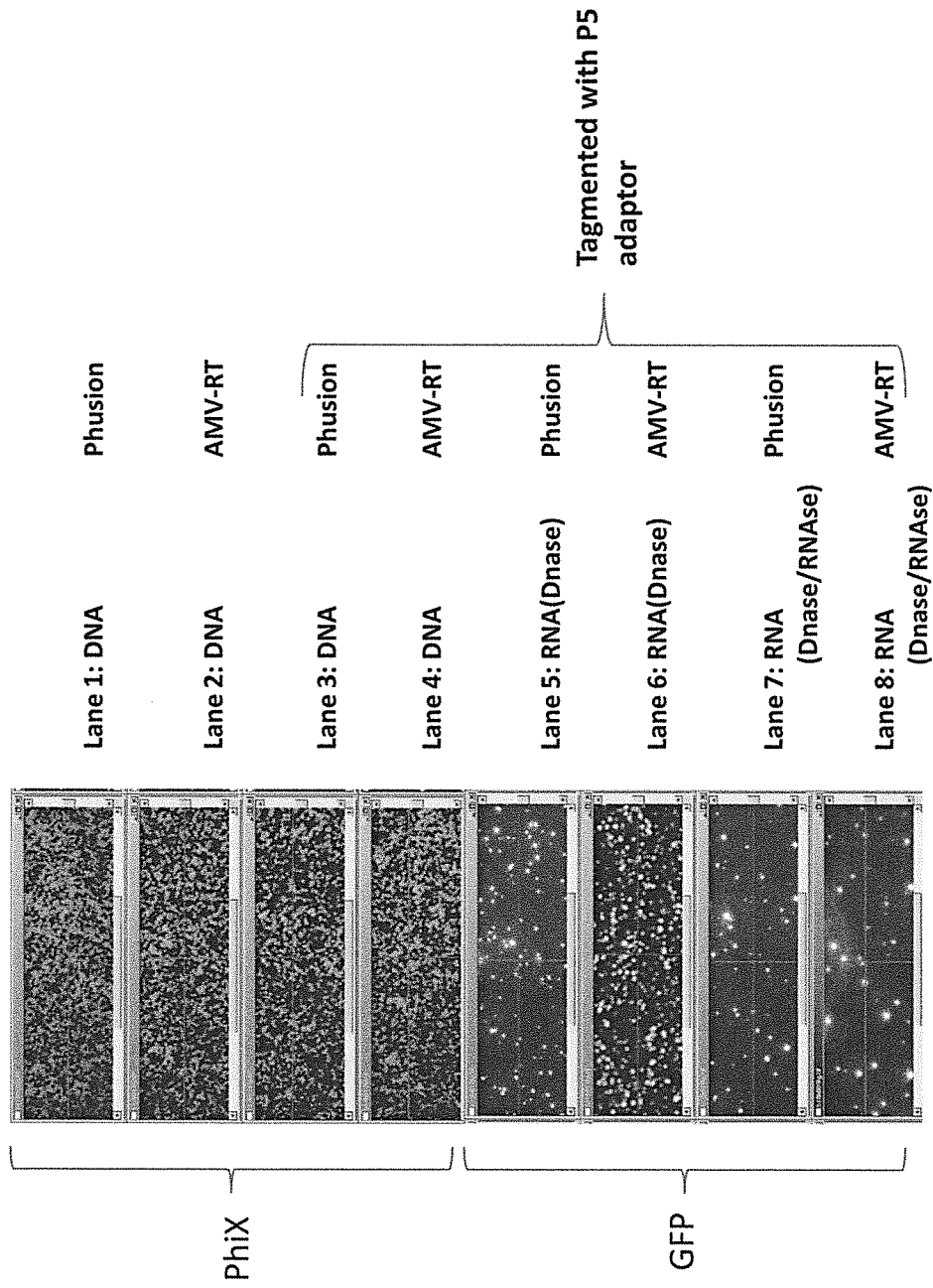

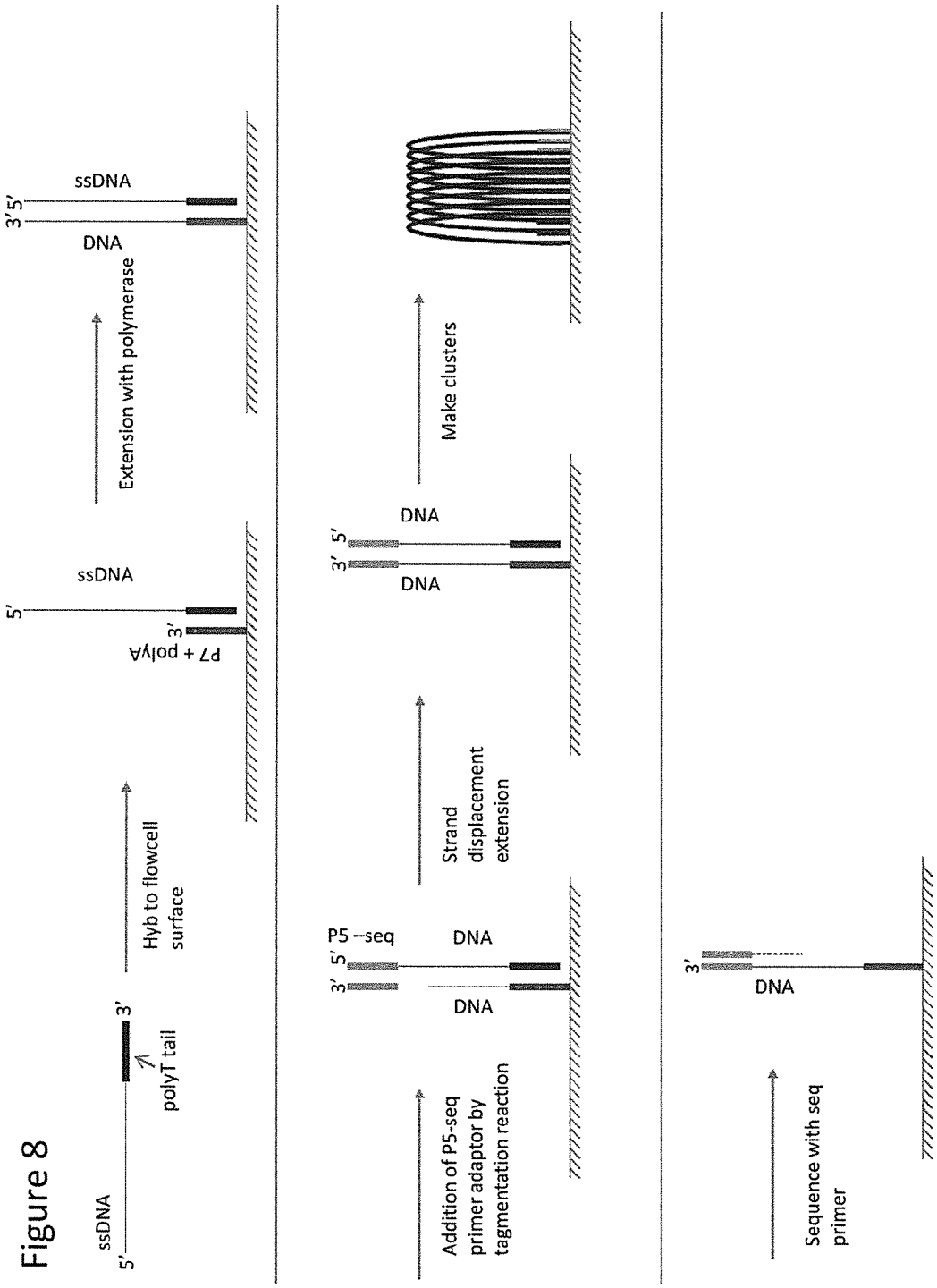

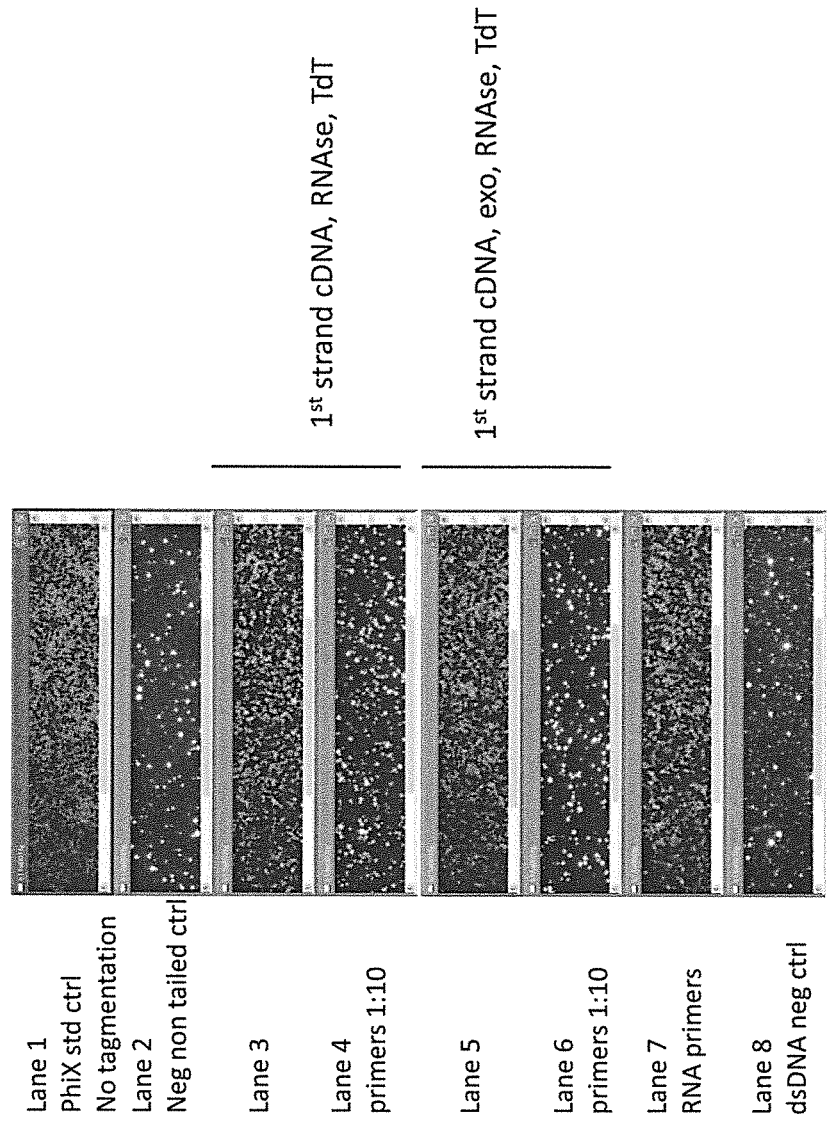

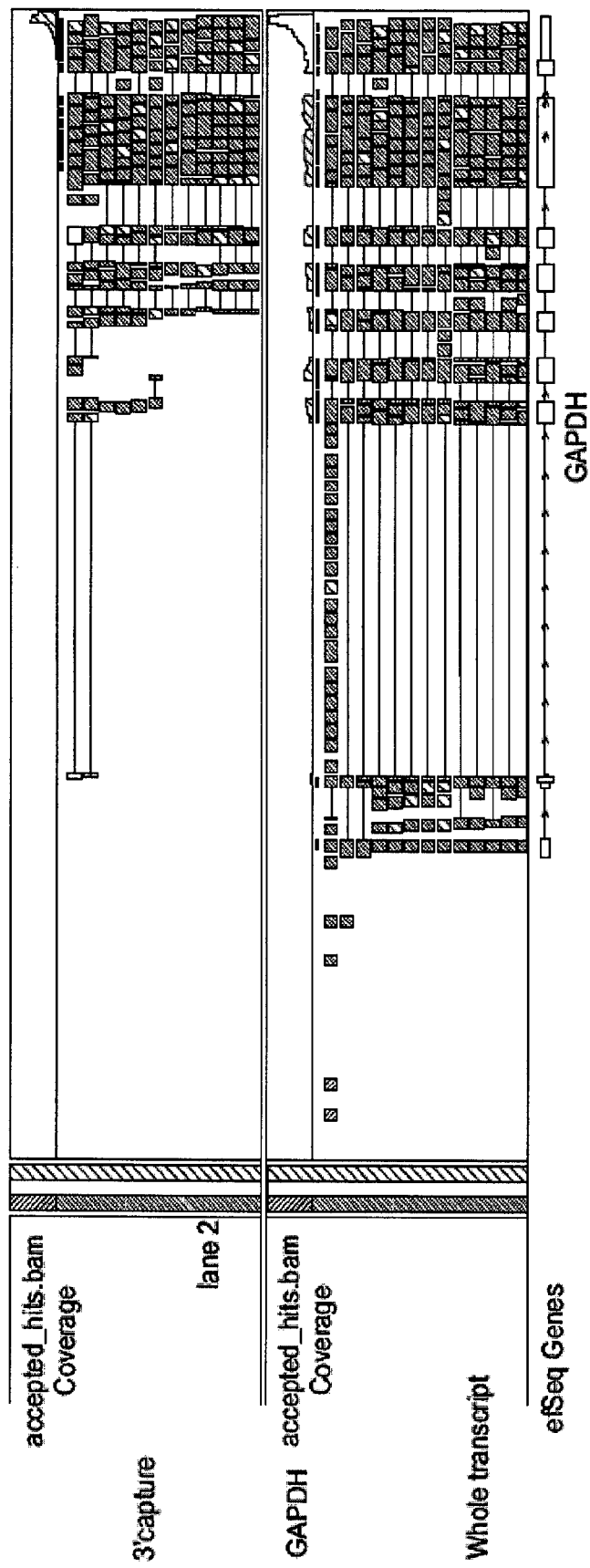

METHODS OF NUCLEIC ACID SEQUENCING

The present application claims priority to U.S. Provisional patent application Ser. No. 61/607,418 filed Mar. 6, 2012, which is incorporated herein by reference in its entirety.

BACKGROUND

Sequencing techniques for sequencing nucleic acids including RNA have been developed. Sequencing techniques include, for example, sequencing-by-synthesis. Sequencing-by-synthesis or cycle sequencing can be accomplished by stepwise addition of nucleotides containing, for example, a cleavable or photobleachable dye label as described, for example, in U.S. Pat. No. 7,427,673; U.S. Pat. No. 7,414,116; WO 04/018497; WO 91/06678; WO 07/123744; and U.S. Pat. No. 7,057,026, the disclosures of which are incorporated herein by reference in their entireties. Alternatively, pyrosequencing techniques may be employed. Pyrosequencing detects the release of inorganic pyrophosphate (PPi) as particular nucleotides are incorporated into the nascent strand (Ronaghi et al., (1996) "Real-time DNA sequencing using detection of pyrophosphate release." *Analytical Biochemistry* 242(1), 84-9; Ronaghi, M. (2001) "Pyrosequencing sheds light on DNA sequencing." *Genome Res.* 11(1), 3-11; Ronaghi, M., Uhlen, M. and Nyren, P. (1998) "A sequencing method based on real-time pyrophosphate." *Science* 281(5375), 363; U.S. Pat. No. 6,210,891; U.S. Pat. No. 6,258,568; and U.S. Pat. No. 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons.

Sequencing techniques also include sequencing by ligation techniques. Such techniques use DNA ligase to incorporate oligonucleotides and identify the incorporation of such oligonucleotides and are described in U.S. Pat. No. 6,969,488; U.S. Pat. No. 6,172,218; and U.S. Pat. No. 6,306,597; the disclosures of which are incorporated herein by reference in their entireties. Other sequencing techniques include, for example, fluorescent in situ sequencing (FISSEQ), and Massively Parallel Signature Sequencing (MPSS).

Preparation of DNA samples for sequencing can be relatively straightforward and include using transposition reactions to fragment and add adaptor sequences to the DNA fragments, which simplifies the sample preparation process. See, e.g., International Publication No. WO 2010/048605, which is incorporated by reference herein in its entirety. By contrast, current protocols for sequencing RNA samples employ a sample preparation method that converts the RNA in the sample into a double-stranded cDNA format prior to sequencing. Thus, preparation of RNA samples for sequencing is more labor intensive. In addition, current protocols are less than optimal in their ability to preserve strand-specific information. More specifically, most methods are not able to preserve strand information about the direction of the original single-stranded RNA molecule after being converted into double stranded cDNA. Preserving strand-specific information is important for annotation of new genes and for determining gene expression levels. Some methods attempt to preserve strand specific information by ligating adaptors to the ends of single-stranded RNA molecules. The adaptors can have sequences that provide distinguishable information for both ends of the double stranded cDNA generated from the RNA molecules. However, this method has disadvantages. For example, if the RNA molecules are fragmented, after fragmentation the internal parts of the molecules lose their directional (i.e., strand specific) information.

SUMMARY

Provided herein is a method of tagging DNA:RNA duplexes. The method includes the steps of providing a transposase and a transposon composition, providing one or more DNA:RNA duplexes immobilized on a support, and contacting the transposase and transposon composition with the one or more DNA:RNA duplexes under conditions wherein the one or more DNA:RNA duplexes and transposon compositions undergo a transposition reaction to produce one or more tagged DNA:RNA duplexes, wherein the transposon composition comprises a double stranded nucleic acid molecule comprising a transferred strand and a non-transferred strand. The method can also be performed for tagging DNA:DNA duplexes that are immobilized on a solid support.

The details of one or more embodiments are set forth in the accompanying drawings and the description below. Other features, objects, and advantages will be apparent from the description and drawings, and from the claims.

DESCRIPTION OF DRAWINGS

FIG. 6 shows pictures of clusters stained with SYBR green. Lanes 1-4 contained PhiX DNA and Lanes 5-8 contained GFP RNA. Lanes 5 and 6 contained RNA that was pre-treated with DNase to remove DNA. Lanes 7 and 8 contained RNA that was pre-treated with DNase and treated with RNase as an additional control. First extension was carried out using either Avian Myeloblastosis Virus Reverse Transcriptase (AMV-RT) (Lanes 2, 4, 6 and 8) or Phusion DNA polymerase (Lanes 1, 3, 5, and 7). Lanes 3-8 were tagmented with P5 adaptor. Isothermal cluster amplification was carried out as standard and the clusters stained with SYBR green.

FIG. 8 is a schematic showing an exemplary method provided herein for DNA:DNA duplex tagging. Single stranded DNA (ssDNA) is fragmented and the fragments labeled with polynucleotides by terminal deoxynucleotidyl transferase. The fragments are then added to a support and captured via hybridization of the polyT tail with its complement immobilized on the solid support. The hybridized ssDNA molecules are converted to a DNA:DNA duplex with a DNA polymerase. A transposome complex or composition comprising a transposase and an adaptor duplex (i.e., transposon) of a P5-seq sequence is used to tagment the duplex. Following extension of the DNA strand to the end with a strand displacing polymerase, the molecules can be amplified (e.g., cluster amplification) and sequenced.

FIG. 9 shows pictures of clusters stained with SYBR Green from an experiment designed to generate data using a whole mRNA transcript sample. Lane 1 is a PhiX standard library where there is no tagmentation. Lane 2 is a negative control where no tailing was performed and Lane 8 is a dsDNA negative control. Lanes 3 and 4 are the same experiment, except primers were diluted for Lane 4. Lanes 5 and 6 are the same experiment, except primers were diluted for Lane 6. Lane 7 uses random RNA hexamers in lieu of random DNA hexamers.

FIG. 10 shows a picture of the coverage of aligned sequencing reads for GAPDH following the method of FIG. 1. The top 3' capture demonstrates the capture, tagmentation, cluster and sequence alignment from a control polyA tailed mRNA sample. The bottom whole transcript demonstrates mRNA alignment from a mRNA sample that was enriched from a complex total UHR RNA sample, enzymatically fragmented and polyadenylated to demonstrate whole mRNA transcript coverage using the methods of the present disclosure.

DETAILED DESCRIPTION

Current protocols for sequencing RNA samples all employ a sample preparation that converts the RNA in the sample into a double-stranded cDNA format prior to sequencing. Provided herein are methods for sequencing RNA samples that avoids a solution phase preparation of double stranded cDNA intermediate. The provided methods also result in the preservation of strandedness information during sequencing. However, the methods described herein could also be used for labeling and sequencing DNA.

Provided herein is a method of tagging DNA:RNA duplexes. The method includes the steps of providing a transposase and a transposon composition, providing one or more DNA:RNA duplexes immobilized on a support, and contacting the transposase and transposon composition with the one or more DNA:RNA duplexes under conditions wherein the one or more DNA:RNA duplexes and transposon composition undergo a transposition reaction to produce one or more tagged DNA:RNA duplexes. The transposon composition comprises a double stranded nucleic acid molecule comprising a transferred strand and a non-transferred strand. Although the following examples may be exemplified using DNA:RNA duplexes, they could also be amenable for DNA:DNA duplexes where appropriate (see FIG. 8).

Optionally, the one or more DNA:RNA duplexes are tagged on the 5' end of the RNA strand. Optionally, the transferred strand comprises a tag to preserve strand information. The transposition reaction results in a 5' tagged RNA strand comprising the transferred strand of the transposon composition and a gap between the 3' end of the DNA strand and the non-transferred strand of the transposon composition. Optionally, the method further comprises contacting the one or more tagged DNA:RNA duplexes with a nucleic acid modifying enzyme under conditions to extend the 3' end of the DNA stands to copy the RNA strands to their 5' end. The nucleic acid modifying enzyme can displace the non-transferred strand of the transposon composition.

Figure 1:
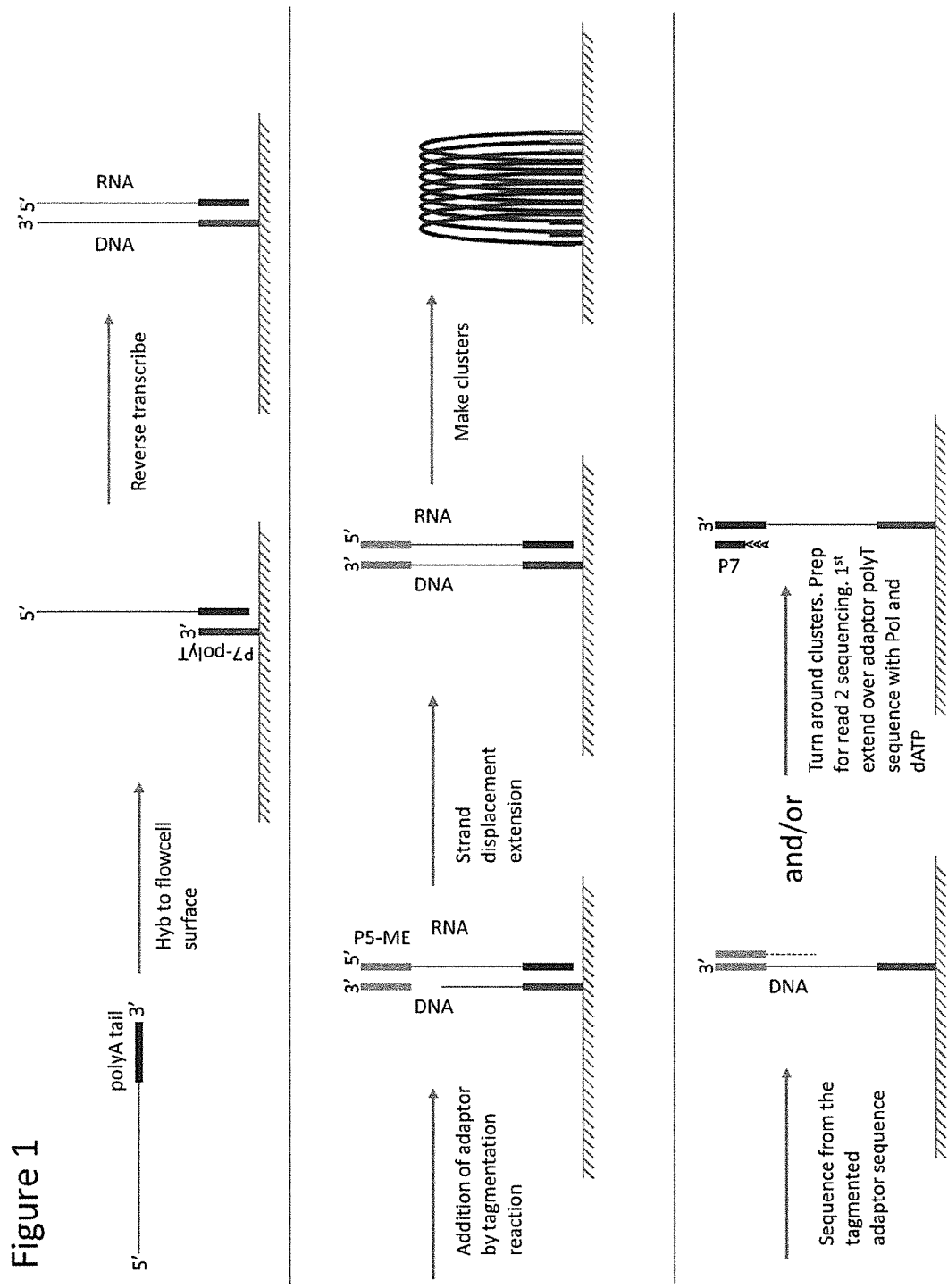
FIG. 1 is a schematic showing an exemplary method provided herein. PolyA tailed mRNA is captured on a support via hybridization to a polyT DNA capture probe or primer coupled to the surface of a support. The polyT strand is next extended with a reverse transcriptase polymerase to make a double stranded molecule comprising a DNA:RNA duplex. Next, a transposome complex (e.g., Tn5 transposase bound with a mosaic end (ME) sequence and sequences complementary to surface amplification primers) is added to the support, which undergoes a transposition reaction with and tagments the duplex, ligating a DNA adaptor oligo to the 5' end of the RNA strand. A strand displacing polymerase (e.g., Bst polymerase) can then be used to extend the 3' end of the DNA strand, displacing the non-transferred strand of the transposome complex and copying the RNA strand to its 5' DNA chimeric end. The double-stranded molecule can then be amplified (e.g., cluster amplification) and sequenced with a sequencing primer. The primer partially comprises the ME sequence and the upstream adaptor sequence. Alternatively, the other end of the molecule (the polyT end) can be sequenced with a primer that anneals upstream of the polyT sequence and is extended with natural dATP nucleotides before commencing cycles of sequence by synthesis (SBS) chemistry.

FIG. 1 is a schematic showing an exemplary method provided herein. Briefly, polyA tailed mRNA is captured on a support (e.g., flowcell) via hybridization to a polyT DNA capture probe (or primer) coupled to the surface of the support. The polyT strand is next extended with a reverse transcriptase polymerase to make a double stranded molecule comprising a DNA:RNA duplex. Next, a transposome complex (e.g., Tn5 bound with a transposon (e.g., mosaic end (ME)) sequence and sequences complementary to surface amplification primers) is added to the support, which 'tagments' the duplex, ligating a DNA adaptor oligo to the 5' end of the RNA strand. A strand displacing polymerase (e.g., Bst polymerase) can then be used to extend the 3' end of the DNA strand, displacing the 'non-transferred strand' of the transposome and copying the RNA strand to its 5' DNA chimeric end. The double-stranded molecule can then be amplified (e.g., clustered) and sequenced with a sequencing primer partially comprising the ME sequence and the upstream adaptor sequence. Alternatively, the other end of the molecule (the polyT end) can be sequenced with a primer that anneals upstream of the polyT sequence and is extended with natural dATP nucleotides before commencing cycles of SBS chemistry. Paired end sequencing is also enabled by this method.

When providing ssDNA for sequencing, a similar approach could be utilized. For example, the 3' end of single stranded DNA polynucleotides could be appended with nucleotides by using terminal deoxynucleotidyl transferase (TdT) and any dNTP such as dATP or dTTP. Any method for appending a string of nucleotides to the end of a ssDNA molecule could be used. FIG. 8 is an example where polyA containing capture probes are immobilized on the support surface and ssDNA-polyT tailed molecules are captured. Any capture sequence, including that of the ssDNA end, could be utilized as long as the complementary sequences are provided by the capture probe on the support and the nucleotides on the ssDNA such that hybridization could occur. Extension of the capture probe to create dsDNA by a DNA polymerase to create a DNA:DNA duplex, transpositional ligation of adaptor oligos and strand displacement amplification as previously described could be performed to provide double stranded molecules for cluster formation. The double-stranded molecule could then be amplified (e.g., cluster amplification) and sequenced.

Figure 2:
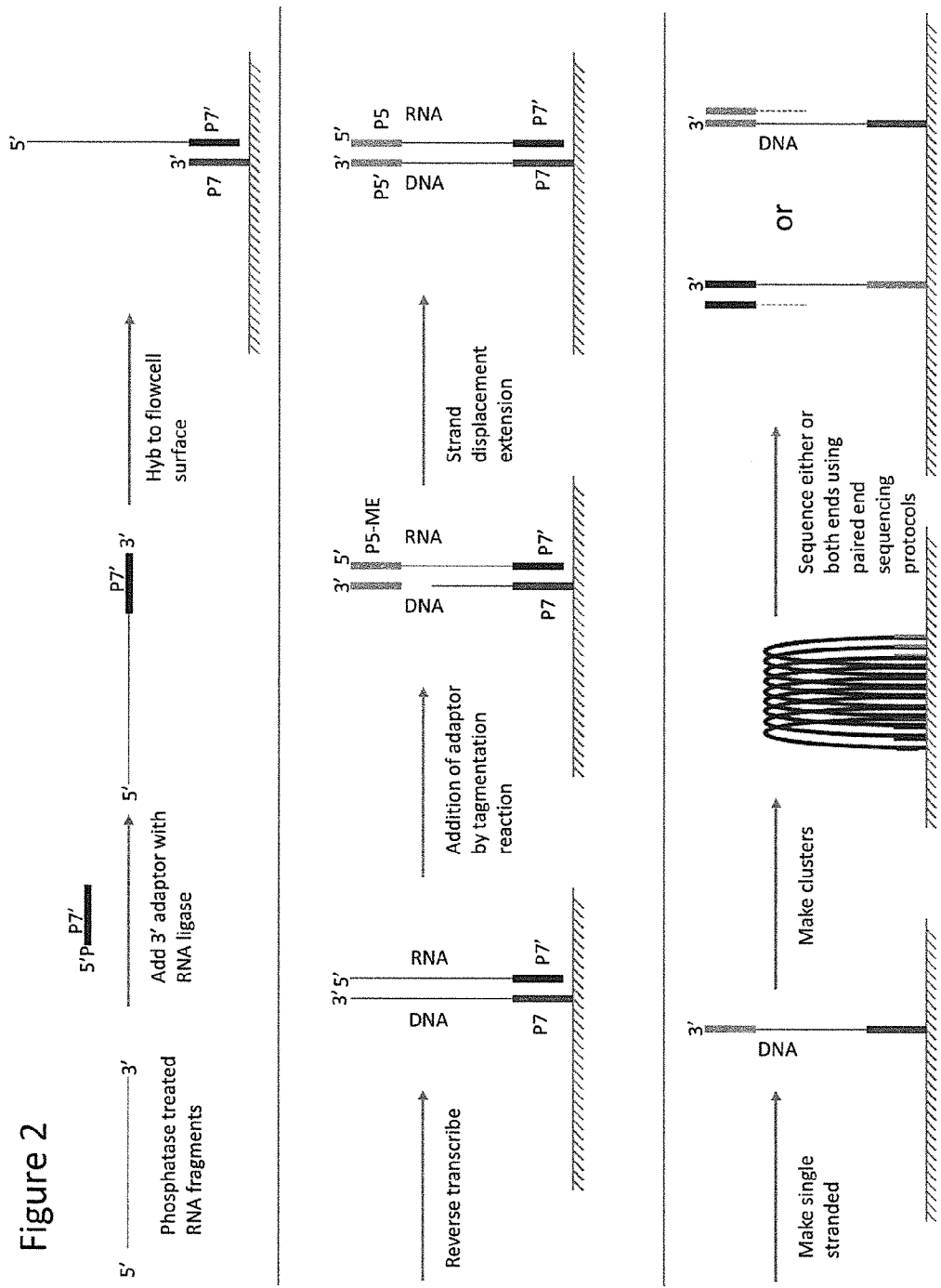
FIG. 2 is a schematic showing an exemplary method provided herein. RNA is fragmented and treated with a phosphatase. A single stranded adaptor molecule is ligated to the 3'end of each RNA fragment comprising the complement of a surface bound primer. The fragments are then added to a support and captured via hybridization. The hybridized RNA molecules are converted to a DNA:RNA duplex with a reverse transcriptase polymerase. A transposome complex or composition comprising a transposase and an adaptor duplex (i.e., transposon) of an ME with P5 is used to tagment the duplex. Following extension of the DNA strand to the end with a strand displacing polymerase, the molecules can be amplified (e.g., cluster amplification) and sequenced.

By way of another example (FIG. 2), RNA (total or polyA enriched) is fragmented, treated with a phosphatase, then a single stranded adaptor molecule is ligated to the 3'end of each fragment comprising the complement of the P7 surface bound primer. The fragments are then added to a support (e.g., flowcell) and captured via hybridization. The hybridized RNA molecules are converted to a DNA:RNA duplex with a reverse transcriptase polymerase. A transposome complex comprising a transposase and an adaptor duplex (e.g., transposon) of a ME sequence with a P5 primer sequence can be used to tagment the duplex. Following extension of the DNA strand to the end with a strand displacing polymerase, the molecules can be amplified and sequenced.

Figure 3:
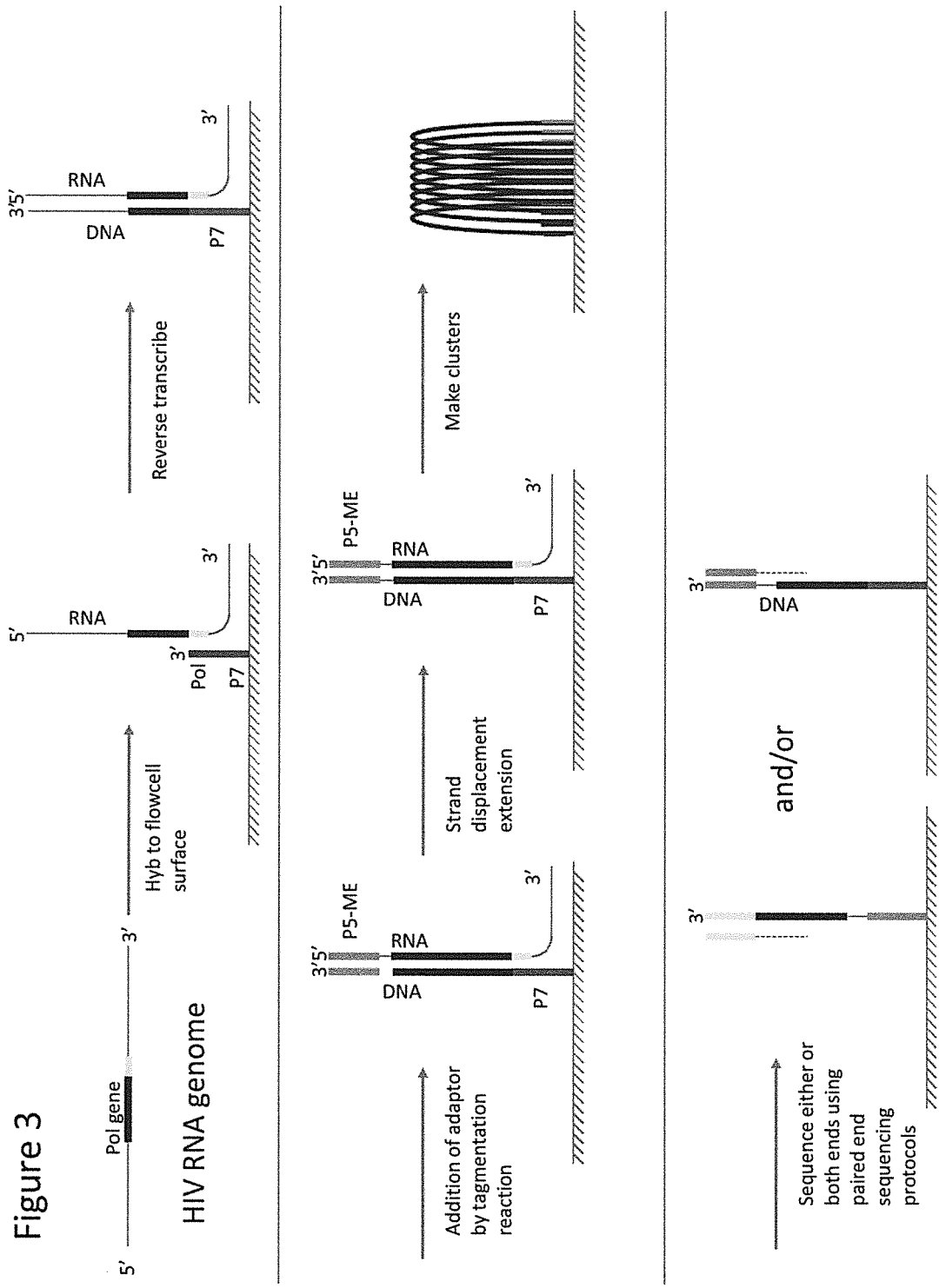
FIG. 3 is a schematic showing an exemplary method provided herein. A support is used that contains two surface grafted primers: a standard grafting primer (e.g., P5) and a modified grafting primer (e.g., P7) that has a target specific capture sequence to its downstream (3') side. An example of a target specific sequence is an oligo sequence complementary to a retroviral reverse transcriptase (e.g., HIV polymerase). Purified viral RNA is added to the support, captured via hybridization, copied with reverse transcriptase and tagmented. Sequencing can be achieved with a primer annealed to the tagmented adaptor or at the other end to the capture probe.

By way of a further example (FIG. 3), a special support (e.g., flowcell) is used that contains two surface grafted primers: a standard grafting primer (e.g., P5) and a modified grafting primer (e.g., P7) that has a target specific capture probe to its downstream (3') side. An example of a target specific probe is an oligo sequence complementary to a retroviral reverse transcriptase (e.g., HIV polymerase). Purified viral RNA is added to a support, captured via hybridization, copied with reverse transcriptase and tagmented. Sequencing can be achieved with a primer annealed to the tagmented adaptor or at the other end to the capture probe. Optionally, the special support contains multiple different target specific capture probes to enable simultaneous capture of many different RNA targets.

The use of an in vitro transposition reaction to tag the target DNA:DNA or DNA:RNA duplexes to generate tagged DNA:DNA or DNA:RNA duplexes involves a transposase, a transposon sequence composition, and suitable reaction conditions.

As used throughout, the term transposon refers to a double-stranded DNA that contains the nucleotide sequences that are necessary to form the complex with the transposase or integrase enzyme that is functional in an in vitro transposition reaction. A transposon forms a complex or a synaptic complex or a transposome complex. The transposon can also form a transposome composition with a transposase or integrase that recognizes and binds to the transposon sequence, and which complex is capable of inserting or transposing the transposon into target DNA with which it is incubated in an in vitro transposition reaction. A transposon exhibits two complementary sequences consisting of a transferred transposon sequence or transferred strand and a non-transferred transposon sequence, or non transferred strand. For example, one transposon that forms a complex with a hyperactive Tn5 transposase (e.g., EZ-Tn5™ Transposase, EPICENTRE Biotechnologies, Madison, Wis., USA) that is active in an in vitro transposition reaction comprises a transferred strand that exhibits a transferred transposon sequence of 5' AGATGTGTATAAGA-GACAG 3', (SEQ ID NO: 1) and a non-transferred strand that exhibits a non-transferred transposon sequence of 5' CTGTCTCTTATACACATCT 3'. (SEQ ID NO: 2). The 3'-end of a transferred strand is joined or transferred to target nucleic acid in an in vitro transposition reaction. The non-transferred strand, which exhibits a transposon end sequence that is complementary to the transferred transposon end sequence, is not joined or transferred to the target nucleic acid in an in vitro transposition reaction. A transposon composition, as used herein, refers to a composition comprising a transposon (i.e., the minimum double-stranded DNA segment that is capable of acting with a transposase to undergo a transposition reaction), optionally including additional sequences. For example, the transposon composition comprises two transposon oligonucleotides containing the transferred transposon oligonucleotide or transferred strand and the non-transferred strand oligonucleotide or non-transferred strand, which, in combination, exhibit the sequences of the transposon. One or both strands can comprise additional sequence. The transposon can include naturally occurring and/or non-naturally occurring nucleotides and natural or non-natural backbone linkages. Optionally, the transposon can also include one or more moieties attached to the one or more nucleotides making up the transposon. For example, one or both strands of the transposon may be biotinylated or may contain a label, for example a fluorescent label.

The terms transferred transposon oligonucleotide and transferred strand are used interchangeably and refer to the transferred portion of both transposons and transposon compositions, i.e., regardless of whether the transposon end is attached to a tag or other sequence or moiety. Similarly, the terms non-transferred transposon oligonucleotide and non-transferred strand are used interchangeably and refer to the non-transferred portion of both transposons and transposon compositions.

In some embodiments, the transposon composition comprises or consists of at least one transposon with one or more other nucleotide sequences in addition to the transposon sequences. Thus, in some embodiments, the transposon composition comprises a transferred strand with one or more other nucleotide sequences 5' of the transferred transposon sequence, e.g., a tag sequence. In addition to the transferred transposon sequence, the tag can have one or more other tag portions or tag domains.

As used herein, a "tag" refers to a nucleic acid component, generally DNA, which provides a means of identifying or addressing a nucleic acid fragment to which it is joined. For example, a tag comprises a nucleotide sequence that permits identification, recognition, and/or molecular or biochemical manipulation of the DNA to which the tag is attached (e.g., by providing a site for annealing an oligonucleotide, such as a primer for extension by a DNA polymerase, by providing an oligonucleotide for capture or for a ligation reaction, or by providing identification of the nucleic acid as originating from a particular source, and the like). The process of joining the tag to a nucleic acid molecule is sometimes referred to herein as "tagging" and nucleic acids that undergoes tagging or that contains a tag is referred to as "tagged" (e.g., "tagged RNA")."

As used throughout, the term strandedness or strand-specific information refers to the preservation of the knowledge about the direction of the original single-stranded molecule. This is preserved in the provided methods since it is known that the DNA strand is complementary to the RNA strand in the DNA:RNA duplexes. Thus, when sequencing the DNA strand, the sequence will be the sequence of the RNA strand preserving the strand-specific information and allowing for correct identification of the RNA molecule and/or its expression level. Methods for preserving strand specific information are also described in WO 2011/003630, which is incorporated by reference herein in its entirety. However, the method described in WO 2011/003630 still requires conversion of the RNA molecules into double-stranded cDNA molecules, which, as described herein, is not as efficient as the methods provided in the present application. Further, the method described in WO 2011/003630 requires a tag in order to preserve strand information. In the methods provided herein, a tag is not required to preserve strand-specific information or strandedness. In embodiments wherein the DNA strand (i.e., first DNA strand) of the DNA:RNA duplexes is amplified to produce first and second amplified DNA strands, strandedness is maintained by the knowledge that the first DNA strand is complementary to the original RNA strand and the second DNA strand is the same sequence as the original RNA strand (with the exception of Ts in the sequence instead of Us). Thus, while a tag (e.g., a tag sequence can be included in the transferred strand of the transposon) can be used to preserve strandedness, it is not required.

As used herein, a tag portion or a tag domain means a portion or domain of a tag that exhibits a sequence for a desired intended purpose or application. One tag portion or tag domain is the transposon domain, which tag portion or tag domain exhibits the transferred transposon sequence. In some embodiments wherein the transferred strand also exhibits one or more other nucleotide sequences, the tag also has one or more other tag domains, each of which tag domains is provided for any desired purpose. For example, a transposon composition can comprise (i) a transferred strand that exhibits one or more additional sequences (in addition to the transposon sequence) can comprise a tag domain selected from among one or more of a restriction site tag domain, a capture tag domain, a sequencing tag domain, an amplification tag domain, a detection tag domain, an address tag domain, and a transcription promoter domain; and (ii) a non-transferred strand that exhibits the non-transferred transposon sequence.

If a description is used for a tag domain, the names and descriptions of different tag domains are for convenience, such as to make it easier to understand and discuss the intended purposes and applications of the different portions or domains of the tag in different embodiments. However, these names and descriptions are not intended to limit the use or applications of the tag or of any of its tag domains in any way. Thus, any particular tag or tag domain can be used for any purpose in addition to, or in place of the intended or primary purpose or application. Also, one tag domain can comprise two or more other tag domains (e.g., a sequencing tag domain can comprise both a capture tag domain and an amplification tag domain) or one tag domain can provide the functions or purposes or applications of two or more different tag domains (e.g., a capture tag domain can also provide the function or purpose of a sequencing tag domain and/or an amplification tag domain for a particular application). Still further, the tag need not be described in terms of one or more different domains in order to be used for any particular purpose or application or function.

As used throughout, the term transposase refers to an enzyme that is capable of forming a functional complex with a transposon-containing composition (e.g., transposons, transposon compositions) and catalyzing insertion or transposition of the transposon-containing composition into the double-stranded target nucleic acid with which it is incubated in an in vitro transposition reaction. A transposase of the provided methods also includes integrases from retrotransposons and retroviruses. Exemplary transposases that can be used in the provided methods include wild-type or mutant forms of Tn5 transposase and MuA transposase.

A "transposition reaction" is a reaction wherein one or more transposons are inserted into target nucleic acids at random sites or almost random sites. Essential components in a transposition reaction are a transposase and DNA oligonucleotides that exhibit the nucleotide sequences of a transposon, including the transferred transposon sequence and its complement (i.e., the non-transferred transposon end sequence) as well as other components needed to form a functional transposition or transposome complex. The method of this invention is exemplified by employing a transposition complex formed by a hyperactive Tn5 transposase and a Tn5-type transposon end or by a MuA or HYPERMu transposase and a Mu transposon end comprising R1 and R2 end sequences (See e.g., Goryshin, I. and Reznikoff, W. S., J. Biol. Chem., 273: 7367, 1998; and Mizuuchi, K., Cell, 35: 785, 1983; Savilahti, H, et al., EMBO J., 14: 4893, 1995; which are incorporated by reference herein in their entireties). However, any transposition system that is capable of inserting a transposon end in a random or in an almost random manner with sufficient efficiency to tag target nucleic acids for its intended purpose can be used in the provided methods. Other examples of known transposition systems that could be used in the provided methods include but are not limited to *Staphylococcus aureus* Tn552, Ty1, Transposon Tn7, Tn/O and IS10, Mariner transposase, Tc1, P Element, Tn3, bacterial insertion sequences, retroviruses, and retrotransposon of yeast (See, e.g., Colegio O R et al., J. Bacteriol., 183: 2384-8, 2001; Kirby C et al., Mol. Microbiol., 43: 173-86, 2002; Devine S E, and Boeke J D., Nucleic Acids Res., 22: 3765-72, 1994; International Patent Application No. WO 95/23875; Craig, N L, Science. 271: 1512, 1996; Craig, N L, Review in: Curr Top Microbiol Immunol., 204: 27-48, 1996; Kleckner N, et al., Curr Top Microbiol Immunol., 204: 49-82, 1996; Lampe D J, et al., EMBO J., 15: 5470-9, 1996; Plasterk R H, Curr Top Microbiol Immunol, 204: 125-43, 1996; Gloor, G B, Methods Mol. Biol., 260: 97-114, 2004; Ichikawa H, and Ohtsubo E., J Biol. Chem. 265: 18829-32, 1990; Ohtsubo, F and Sekine, Y, Curr. Top. Microbiol. Immunol. 204: 1-26, 1996; Brown P O, et al., Proc Natl Acad Sci USA, 86: 2525-9, 1989; Boeke J D and Corces V G, Annu Rev Microbiol. 43: 403-34, 1989; which are incorporated herein by reference in their entireties).

The method for inserting a transposon into a target sequence can be carried out in vitro using any suitable transposon system for which a suitable in vitro transposition system is available or can be developed based on knowledge in the art. In general, a suitable in vitro transposition system for use in the methods of the present invention requires, at a minimum, a transposase enzyme of sufficient purity, sufficient concentration, and sufficient in vitro transposition activity and a transposon with which the transposase forms a functional complex with the respective transposase that is capable of catalyzing the transposition reaction. Suitable transposase transposon sequences that can be used in the invention include but are not limited to wild-type, derivative or mutant transposon sequences that form a complex with a transposase chosen from among a wild-type, derivative or mutant form of the transposase.

In the provided methods, the DNA:RNA duplexes can be provided in a variety of ways. By way of example, the support can comprise a plurality of primers and the DNA:RNA duplexes are provided by hybridizing one or more RNA molecules to the immobilized primers on the support and extending the primers hybridized to the RNA molecules using the RNA molecules as template to produce the one or more DNA:RNA duplexes. Optionally, a plurality of DNA:RNA duplexes are provided by hybridizing a plurality of RNA molecules to the immobilized primers on the support and extending the primers hybridized to the RNA molecules using the RNA molecules as template to produce the plurality of DNA:RNA duplexes.

As stated above, the methods can comprise providing a support with a plurality of primers; the primers or a subset thereof comprising a sequence capable of binding to one or more RNA molecules. For example, the immobilized primers may include a polyT sequence and the RNA may include a polyA sequence capable of hybridizing to the polyT sequence. Alternatively or additionally, the plurality of immobilized primers can include target specific primers capable of hybridizing to one or more of the RNA molecules in the plurality of RNA molecules. Thus, the RNA strand of the one or more DNA:RNA duplexes comprises a sequence complementary to at least a portion of one or more of the immobilized primers. Optionally, the plurality of immobilized primers comprises a first subset of primers of a first sequence and a second subset of primers of a second sequence. The first or second subset of primers may comprise a polyT sequence.

Optionally, a 3' adaptor can be added to the plurality of RNA molecules, the 3' adaptor comprising a sequence complementary to the plurality of immobilized primers or a subset thereof. Such 3'-adaptor ligated RNA molecules can then be hybridized to the immobilized primers.

Thus, the immobilized primers or a subset thereof can comprise a polyT sequence, an RNA target specific sequence or a sequence complementary to an adaptor ligated to the RNA molecule. Optionally, the plurality of primers comprises at least two subsets of primers, the first subset comprising a polyT sequence, an RNA target specific sequence or a sequence complementary to an adaptor ligated to the RNA molecule, and the second subset of primers comprising a sequence that is capable of binding to a sequence on the DNA strand of the DNA:RNA duplexes. Such a sequence can be, for example, the same sequence as a sequence of the transferred strand of the transposon. As described throughout, after transposition, there will be a gap between the end of the DNA strand and the non-transferred strand of the transposon. The DNA strand can then be extended to copy the RNA strand. The copying will include copying the sequences of the transferred strand of the transposon. The DNA strand will then include sequences complementary to the sequences of the transferred strand of the transposon and, thus, the primers or subset thereof on the surface of the support. In other words, if one or more of the primers comprises a sequence the same as or similar to the transferred strand of the transposon, the DNA strand in the DNA:RNA duplexes will then be capable of hybridizing to the primers since the DNA strand contains a sequence complementary to the primer.

Suitable nucleic acid modifying enzymes capable of extending the 3' end of the DNA strands to copy the RNA strands to their 5' end and displacing the non-transferred strand of the transposon are known. Briefly, some DNA polymerases are able to displace the strand complementary to the template strand as a new DNA strand is synthesized by the polymerase. This process is called strand displacement and the DNA polymerases that have this activity are referred to herein as strand-displacing DNA polymerases. In general, a DNA-template-specific DNA polymerase used for the provided methods efficiently synthesizes DNA of a suitable length for the intended purpose without disengaging from the template (or terminating synthesis of the DNA), which is referred to as the enzyme's processivity. The capability of a DNA polymerase to strand displace can be readily determined using the polymerase in a rolling circle replication assay as described by Fire and Xu (Proc. Natl. Acad. Sci. USA 92: 4641-4645, 1995), which is incorporated by reference herein in its entirety. Strand displacement and DNA polymerase processivity can also be assayed using methods described in Kong et al. (J. Biol. Chem. 268: 1965-1975, 1993), which is incorporated by reference herein in its entirety. Terminal transferase is also defined as a DNA polymerase herein, which DNA polymerase is used as a composition in some embodiments of the provided methods. Terminal transferase can be used because it catalyzes template-independent addition of dNTPs to the 3'-hydroxyl termini of DNA.

In the methods provided herein, the method can further comprise sequencing at least a portion of the DNA strands and/or amplifying at least a portion of the DNA strands. Optionally, the RNA strands from the DNA:RNA duplexes can be removed prior to sequencing and/or amplification. By way of example, the method further comprises removing the RNA strands from the DNA:RNA duplexes and sequencing at least a portion of the DNA strands (i.e., the first DNA strands). The method can also include copying at least a portion of the DNA strands to produce a second DNA strand complementary to the DNA strand (i.e., the first DNA strand) of the DNA:RNA duplexes. The second complementary DNA strand can then be sequenced, if desired. Optionally, the first DNA strand of the DNA:RNA duplexes can be removed prior to sequencing the second complementary DNA strand.

In the provided methods, optionally, after removal of the RNA strand from the DNA:RNA duplexes, the DNA strands may be amplified to produce a plurality of double stranded DNA molecules comprising first and second amplified strands. Optionally, the amplification produces a cluster, described in more detail below.

In some embodiments, when the DNA strands have been amplified to produce a plurality of double stranded DNA molecules, either one or both of the strands can be sequenced. By way of example, the methods can include removing the first amplified strands followed by sequencing at least a portion of the second amplified strands. Optionally, the first amplified strands can be regenerated by copying at least a portion of the second amplified strands. The second amplified strands can then be removed in order to sequence at least a portion of the first amplified strands. Optionally, sequence reads of a portion or all of one or both of the first and second amplified strands can be performed without removing all or a portion of either strand.

Various protocols can be used to generate amplified nucleic acids, for example, nucleic acids amplified on a support. For example, nucleic acids can be amplified by emulsion PCR, or bridge PCR (Mitra & Church *Nucleic Acids Res.* 27, e34 (1999); Dressman et al. *Proc. Natl. Acad. Sci. USA* 100, 8817-8822 (2003); Adessi, C. et al. *Nucleic Acids Res.* 28, e87 (2000); Fedurco et al. *Nucleic Acids Res.* 34, e22 (2006), each of which is incorporated herein by reference).

In embodiments using emulsion PCR, nucleic acids can be PCR amplified in a water-in-oil emulsion. In one embodiment, a single primer pair is used. One of the PCR primers is tethered to the surface (5'-attached) of a support (e.g., micron-scale beads) and the other primer is in solution. Optionally, the support comprises primers of more than one sequence, the primers being target specific primers capable of hybridizing to one or more target RNA molecules and the primer in solution is of the same sequence (e.g., a sequence complementary to the sequence added to the DNA strand by copying the tagged RNA strand to its 5' end). Generally, a low template concentration results in most bead-containing compartments having either zero or one template molecule present. In productive emulsion compartments (where both a bead and template molecule is present), RNA molecules can be captured and/or the corresponding DNA complement of the RNA molecule amplified at the surface of the bead. After breaking the emulsion, beads bearing amplification products can be selectively enriched. Each clonally amplified bead will bear on its surface PCR products corresponding to amplification of a single molecule from the template library. Various embodiments of emulsion PCR methods that are useful are set forth in U.S. Pat. App. Publ. Nos. 2005/0042648 A1; 2005/0079510 A1 and 2005/0130173 A1, and WO 05/010145, each of which is incorporated herein by reference.

In embodiments using bridge PCR, also known as cluster formation, nucleic acids from a template library can be amplified using primers coated on the surface of a support. The primers can be attached at their 5' ends by a flexible linker. Amplification products originating from any given member of the template library remain locally tethered near the point of origin. At the conclusion of the PCR, each clonal cluster contains several copies of a single member of the template library. In the provided methods, each DNA:RNA duplex forms the origin of a clonal cluster. Upon removal of the RNA strand, the DNA strand can be copied using the primers attached to the support to generate amplified copies of the DNA strand and to produce the clonal cluster. Various embodiments of bridge PCR methods that are useful are set forth in U.S. Pat. App. Publ. No. 2007/0128624 A1, WO 07/010251, U.S. Pat. No. 6,090,592 and U.S. Pat. No. 5,641,658, each of which is incorporated herein by reference. Methods for carrying out amplification are also described in U.S. Publication No. 2009/0226975; WO 98/44151; WO 00/18957; WO 02/46456; WO 06/064199; and WO 07/010251; which are incorporated by reference herein in their entireties.

The methods set forth herein can make or use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

As used herein, the term "nucleic acid" can be used refer to at least two nucleotide analog monomers linked together. A nucleic acid can contain phosphodiester bonds, however, in some embodiments, a nucleic acid can be an analog having other types of backbones, comprising, for example, phosphoramide, phosphorothioate, phosphorodithioate, peptide nucleic acid backbones and linkages, positive backbones, or non-ionic backbones. A nucleic acid can include a pentose moiety such as ribose (present in naturally occurring RNA), deoxy-ribose (present in naturally occurring DNA) or dideoxy ribose. In some embodiments a nucleic acid can have a non-pentose moiety or carbocyclic sugar instead of a ribose or deoxyribose moiety. A nucleic acid can have one or more different base moieties including, but not limited to, adenine (A), guanine (G), thymine (T), uracil (U), cytosine (C), inosine, xanthanine, hypoxanthanine, isocytosine, isoguanine, nitropyrrole (including 3-nitropyrrole) and/or nitroindole (including 5-nitroindole). A nucleic acid used herein can include native or non-native bases. Thus, a nucleic acid can include naturally occurring and/or non-naturally occurring nucleotides and natural or non-natural backbone linkages. Nucleic acids may be single stranded or double stranded, as specified, or contain portions of both double stranded and single stranded sequence. The nucleic acid may be DNA (e.g. genomic DNA or cDNA), RNA or a hybrid.

As used herein, the term "array" means a population of different molecules that are attached to one or more supports such that the different molecules can be differentiated from each other according to their relative location. An array can include different molecules that are each located at a different addressable location (e.g. a feature) on a support. Alternatively, an array can include separate supports each bearing a different molecule, wherein the different probe molecules can be identified according to the locations of the supports on a surface to which the supports are attached or according to the locations of the supports in a liquid such as a fluid stream. The molecules of the array can be, for example, nucleic acid primers, nucleic acid probes, nucleic acid templates or nucleic acid enzymes such as polymerases. For example, in particular embodiments target nucleic acids can be attached to a surface of a detector or to a layer (e.g. an acrylamide layer) that is present at the surface of the support. Hydrogels are particularly useful such as those set forth in US Pat. Pub. No. 2011/0059865 A1, which is incorporated herein by reference.

As used herein the term "array of nucleic acids" means a solid support having a plurality of spatially distinguishable nucleic acids disposed thereon or therein. The nucleic acids can be disposed in an ordered or random pattern of features. An individual feature can be, for example, a spatially isolated nucleic acid molecule, or an ensemble of nucleic acid molecules such as a cluster. An array can be a composite array comprising a plurality of individual arrays configured to allow processing of multiple samples. The individual arrays, referred to herein as "sub-arrays," include groups of nucleic acid features. Sub-arrays appear in distinct regions with in a larger array. The sub-arrays themselves can be ordered or non-ordered. Such sub-arrays can be optionally spatially addressable. Sub-arrays can include clusters of identical nucleic acids. An example of a composite array composed of individual sub-arrays is a microtiter plate having wells in which the plate as a whole is an array of nucleic acids (or composite array) while each individual well represents a sub-array within the larger composite array.

As used herein the term "support" refers to a substrate for immobilizing an array of nucleic acids. A "support" is a material having a rigid or semi-rigid surface to which a nucleic acid array can be attached or upon which nucleic acids can be synthesized and/or modified. Supports can include any resin, microbead, glass, controlled pore glass (CPG), polymer support, membrane, paper, plastic, plastic tube or tablet, plastic bead, glass bead, slide, ceramic, silicon chip, multi-well plate, nylon membrane, fiber optic, and PVDF membrane.

A support can include any flat wafer-like substrates and flat substrates having wells, such as a microtiter plate, including 96-well plates. Exemplary flat substrates include chips, slides, etched substrates, microtiter plates, and flow cell reactors, including multi-lane flow cell reactors having multiple microfluidic channels, such as the eight channel flow cell used in the cBot sequencing workstation (Illumina, Inc., San Diego, Calif.). Exemplary flow cells that can be used are also described in WO 2007/123744, which is incorporated herein by reference in its entirety.

A support can also include beads, including magnetic beads, hollow beads, and solid beads. Beads can be used in conjunction with flat supports, such flat supports optionally also containing wells. Beads, or alternatively microspheres, refer generally to a small body made of a rigid or semi-rigid material. The body can have a shape characterized, for example, as a sphere, oval, microsphere, or other recognized particle shape whether having regular or irregular dimensions. The sizes of beads, in particular, include, without limitation, about 1 µm, about 2 µm, about 3 µm, about 5 µm, about 10 µm, about 20 µm, about 30 µm, about 40 µm, about 60 µm, about 100 µm, about 150 µm or about 200 µm in diameter. Other particles can be used in ways similar to those described herein for beads and microspheres.

The composition of a support can vary, depending for example, on the format, chemistry and/or method of attachment and/or on the method of nucleic acid synthesis. Support materials that can be used in accordance with the present disclosure include, but are not limited to, polypropylene, polyethylene, polybutylene, polyurethanes, nylon, metals, and other suitable materials. Exemplary compositions include supports, and chemical functionalities imparted thereto, used in polypeptide, polynucleotide and/or organic moiety synthesis. Such compositions include, for example, plastics, ceramics, glass, polystyrene, melamine, methylstyrene, acrylic polymers, paramagnetic materials, thoria sol, carbon graphite, titanium dioxide, latex or cross-linked dextrans such as Sepharose™, cellulose, nylon, cross-linked micelles and Teflon™, as well as any other materials which can be found described in, for example, "*Microsphere Detection Guide*" from Bangs Laboratories, Fishers Ind., which is incorporated herein by reference. A support particle can be made of cross-linked starch, dextrans, cellulose, proteins, organic polymers including styrene polymers including polystyrene and methylstyrene as well as other styrene co-polymers, plastics, glass, ceramics, acrylic polymers, magnetically responsive materials, colloids, thoriasol, carbon graphite, titanium dioxide, nylon, latex, or TEFLON®. "Microsphere Detection Guide" from Bangs Laboratories, Fishers, Inc., hereby incorporated by reference in its entirety, is a helpful guide. Further exemplary supports within the scope of the present disclosure include, for example, those described in US Application Publication No. 2002/0102578 and U.S. Pat. No. 6,429,027, both of which are incorporated herein by reference in their entirety.

Attachment of a nucleic acid to a support, whether rigid or semi-rigid, can occur via covalent or non-covalent linkage(s). Exemplary linkages are set forth in U.S. Pat. Nos. 6,737,236; 7,259,258; 7,375,234 and 7,427,678; and US Pat. Pub. No. 2011/0059865 A1, each of which is incorporated herein by reference. In some embodiments, a nucleic acid or other reaction component can be attached to a gel or other semisolid support that is in turn attached or adhered to a solid-phase support. In such embodiments, the nucleic acid or other reaction component will be understood to be solid-phase.

Optionally, the support is a bead or a plurality of beads. Optionally, the support is a planar support. Optionally, a plurality of beads is provided, each bead comprising one or more DNA:RNA duplexes. If a bead comprises more than one DNA:RNA duplex, the duplexes can be of the same sequence or different sequence. Optionally, a plurality of beads is provided each bead comprising a DNA:RNA duplex. The beads in the plurality of beads can comprise the same or a different DNA:RNA duplex. For example, a first subset of beads in the plurality of beads can comprise a DNA:RNA duplex of a first sequence while a second subset of beads in the plurality of beads can comprise a DNA:RNA duplex of a second sequence.

Any of a variety of sequencing protocols and respective reagents can be used in any method or device set forth herein. Sequencing-by synthesis (SBS) techniques generally involve the enzymatic extension of a nascent nucleic acid strand through the iterative addition of nucleotides against a template strand. SBS can utilize nucleotide monomers that have a terminator moiety or those that lack any terminator moieties. Methods utilizing monomers having terminators include, for example, those described in WO 04/018497, U.S. Pat. No. 7,057,026, WO 91/106678, WO 07/123744, US 2007/0166705, US 2006/0188901, US 2006/0240439, US 2006/0281109, WO 05/065814, US 2005/0100900, WO 06/064199 or WO 07010251, the disclosures of which are incorporated herein by reference in their entireties. Also useful are SBS methods that are commercially available from Illumina, Inc., San Diego Calif.

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate or protons; or the like. The different nucleotides can be distinguishable from each other, or alternatively, the two or more different labels can be indistinguishable under the detection techniques being used. For example, the different nucleotides present in a sequencing reagent can have different labels and they can be distinguished using appropriate optics as exemplified by the sequencing methods developed by Solexa (now Illumina, Inc.). However, it is also possible to use the same label for the two or more different nucleotides present in a sequencing reagent or to use detection optics that do not necessarily distinguish the different labels.

Methods utilizing nucleotide monomers lacking terminators are also useful including, for example, pyrosequencing. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. No. 6,210,891; U.S. Pat. No. 6,258,568 and U.S. Pat. No. 6,274,320, the disclosures of which are incorporated herein by reference in their entireties). In pyrosequencing, released PPi can be detected by being converted to adenosine triphosphate (ATP) by ATP sulfurylase, and the level of ATP generated is detected via luciferase-produced photons.

Some embodiments can utilize sequencing by ligation techniques. Such techniques utilize DNA ligase to incorporate oligonucleotides. Exemplary SBS systems and methods which can be utilized with the methods and systems described herein are described in U.S. Pat. No. 6,969,488, U.S. Pat. No. 6,172,218, and U.S. Pat. No. 6,306,597, the disclosures of which are incorporated herein by reference in their entireties.

Some embodiments can utilize methods involving the real-time monitoring of DNA polymerase activity. Nucleotide incorporations can be detected through fluorescence resonance energy transfer (FRET) interactions between a fluorophore-bearing polymerase and y-phosphate-Labeled nucleotides as described, for example, in U.S. Pat. No. 7,329,492 and U.S. Pat. No. 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. No. 7,405,281 and U.S. Patent Application Publication No. 2008/0108082 (each of which is incorporated herein by reference). The illumination can be restricted to a zeploliter-scale volume around a surface-tethered polymerase such that incorporation of fluorescently labeled nucleotides can be observed with low background (Levene, M. I. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nanostructures." Proc. Nat'l. Acad. Sci. USA 105, 1176-1181 (2008), the disclosures of which are incorporated herein by reference in their entireties).

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation may not be explicitly disclosed, each is specifically contemplated and described herein. For example, if a method is disclosed and discussed and a number of modifications that can be made to the method steps are discussed, each and every combination and permutation of the method steps, and the modifications that are possible are specifically contemplated unless specifically indicated to the contrary. Likewise, any subset or combination of these is also specifically contemplated and disclosed. This concept applies to all aspects of this disclosure. Thus, if there are a variety of additional steps that can be performed it is understood that each of these additional steps can be performed with any specific method steps or combination of method steps of the disclosed methods, and that each such combination or subset of combinations is specifically contemplated and should be considered disclosed.

Throughout this application, various publications are referenced. The disclosures of these publications in their entireties are hereby incorporated by reference into this application.

A number of embodiments have been described. Nevertheless, it will be understood that various modifications may be made. Accordingly, other embodiments are within the scope of the following claims.

EXAMPLES

Example 1

RNA Sequencing Employing a Tagmentation Reaction of a DNA:RNA Duplex

Figure 4:
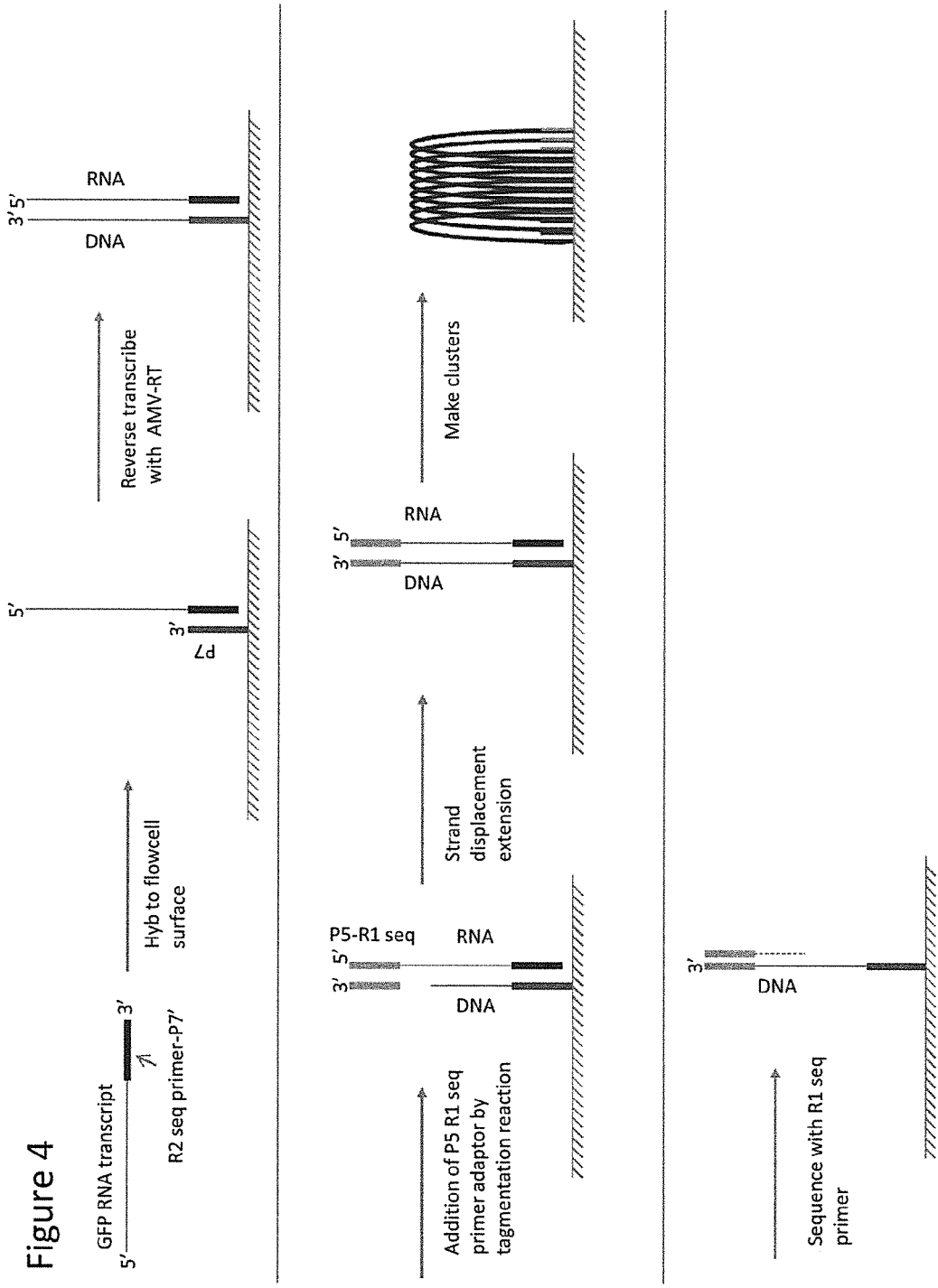
FIG. 4 is a schematic showing an exemplary method provided herein. RNA transcripts are generated from a plasmid containing green fluorescent protein (GFP) transcript sequence and a sequence complementary to a surface bound primer (e.g., P7' sequence). The transcripts are hybridized to a support comprising primers comprising, for example, a P7 sequence. The hybridized RNA molecules are converted to a DNA:RNA duplex with a reverse transcriptase polymerase. A transposome complex is used to tagment the duplex. Following extension of the DNA strand to the end with a strand displacing polymerase and removal of the RNA strand, the molecules can be amplified (e.g., cluster amplification) and sequenced.

An exemplary experiment with a P7' adapted RNA transcript was performed, the schematic of which is outlined in FIG. 4. RNA transcripts were generated from a plasmid containing Green Fluorescent Protein (GFP) using the Riboprobe® In vitro Transcription System kit from Promega (Madison, Wis.) following manufacturer's protocol.

The sequence of the GFP expression cassette is shown below (SEQ ID NO:3).

```
                                            (SEQ ID NO: 3)
aatgatacggcgaccaccgagatctacactctttccctacacgacgctct tccgatcttaatacgactcactataggcaattttaactttactaaggaga attcaccatgaaacatcaccatcaccacacGACTACAAAGACGATGACG ACAAGgcgatcgtgagcaagggcgaggagctgttcaccggggtggtgccc atcctggtcgagctggacggcgacgtaaacggccacaagttcagcgtgtc cggcggggcgagggcgatgccacctacggcaagctgaccctgaagttcat ctgcaccaccggcaagctgcccgtgccctggcccacccctcgtgaccaccc tgacctacggcgtgcagtgcttcagccgctacccgaccacatgaagcagc acgacttcttcaagtccgccatgcccgaaggctacgtccaggagcgcacc atcttcttcaaggacgacggcaactacaagacccgcgccgaggtgaagtt cgagggcgaaccctggtgaaccgcatcgagctgaagggcatcgacttcaa ggaggacggcaacatcctggggcacaagctggagtacaactacaacagcc acaacgtctatatcatggccgacaagcagaagaacgcatcaaggtgaact tcaagatccgccacaacatcgaggacggcagcgtgcagctcgccgaccac taccagcagaacacccccatcggcgacggccccgtgctgctgcccgacaa ccactacctgagccccagtccgccctgagcaaagacccaacgagaagcg cgatcacatggtcctgctggagttcgtgaccgccgcgggatcactctcg gcatggacgagctgtacaagtaactgctgccaccgctgagaataa ctagcataaccccttggggcctctaaacgggtcttgaggggttttttg agatcggaagagcggttcagcaggaatgccgagaccgatcTCGTATGCCG

TCTTCTGCTTG
```

The pMA-T based plasmid contains P5 (underlined), a T7 polymerase promoter (in bold font), a start codon (in bold font and italics), a His tag (in italics and underlined), a FLAG tag (in capital letters), the GFP sequence, a TAA stop codon (underlined and in bold font), a T7 terminator (in bold font, italics and underlined) and P7' (in capital letters and bold font).

Figure 5:
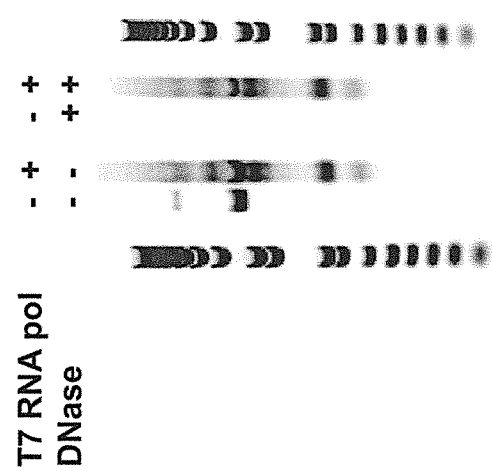
FIG. 5 is a picture of a gel showing RNA transcripts generated from a plasmid containing Green Fluorescent Protein (GFP) and, optionally, treated with DNase to remove the DNA (i.e., plasmid). No residual DNA (i.e., plasmid) was visible following DNase treatment of the RNA transcript.

The RNA transcript should extend from the promoter sequence to the T7 termination sequence. However, the T7 terminator does not stop transcription completely and so some of the resulting RNA transcripts are His_FLAG-_GFP_P7'. The RNA transcript was treated with DNase to remove DNA that would otherwise form clusters. In order to check that the DNase treatment was effective, a reaction was performed and analyzed on a gel to prove that the DNase treatment was effective at removing the DNA. No residual DNA (i.e., plasmid) was visible following DNase treatment of the RNA transcript (FIG. 5).

A PhiX DNA library and the DNase treated GFP-P7' RNA transcripts were hybridized onto different lanes of a flowcell following the standard cluster protocol for template hybridization. Lanes 1-4 contained the PhiX DNA and lanes 5-8 contained the GFP RNA. Lanes 5 and 6 contained RNA that was pre-treated with DNase to remove DNA. Lanes 7 and 8 contained RNA that was pre-treated with DNase and treated with RNase on the flowcell as an additional control. The PhiX DNA library can hybridize via P5 or P7 as both sequences and their complements are present in the template. In contrast, the GFP-P7' RNA templates hybridize to the P7 surface primers only because of their 'strandedness' and the lack of a P5 sequence.

First extension was carried out using either Avian Myeloblastosis Virus Reverse Transcriptase (AMV-RT) (Lanes 2, 4, 6 and 8) or Phusion DNA polymerase (Lanes 1, 3, 5, and 7). AMV-RT can generate a cDNA strand from either an RNA or DNA template, whereas Phusion can only generate a DNA strand from a DNA template.

Some lanes were transposed using a transposome complex containing the transposon sequence P5 adaptor sequence (Lanes 3-8). Gaps in the DNA sequence left after the transposition event were filled in using a strand displacement extension reaction containing Bst DNA polymerase. The transposition event is required in the lanes containing GFP_P7' RNA to add the P5 adapter to generate a template that can make clusters. Isothermal cluster amplification was carried out as standard and the clusters stained with SYBR Green. Pictures of the clusters are shown in FIG. 6.

Lane 1 was a control for cluster generation as it contains a standard format DNA sample extended with PHUSION DNA Polymerase. Successful cluster generation resulted as shown in FIG. 6.

Lane 2 demonstrated that DNA templates can be successfully extended by a reverse transcriptase (generating a DNA:DNA duplex) and make clusters under standard conditions (FIG. 6).

Lanes 3 and 4 demonstrated that the DNA:DNA duplexes (extended with either PHUSION DNA Polymerase or AMV-RT) can be tagmented with a Tn5 adaptor and generate clusters (FIG. 6).

Lane 5 would not be expected to generate clusters because PHUSION DNA Polymerase has been previously reported not to extend opposite an RNA strand. The small number of clusters observed may be due to residual DNA template used to generate the RNA despite DNase treatment, or some degree of extension by PHUSION DNA Polymerase of DNA opposite RNA (FIG. 6).

Lanes 7 and 8 would not be expected to exhibit any cluster formation because the templates have been RNase and DNase treated. As was seen in lane 5, the small number of clusters observed may be due to residual DNA template used to generate the RNA despite DNase treatment (FIG. 6).

Lane 6 of FIG. 6 demonstrates extension of a DNA strand against an RNA template as expected. These extended templates were not expected to form clusters since they do not possess a P5 sequence. However, following tagmentation with a P5 adaptor (q.e.d lane 6), they form clusters. The small number of clusters in lanes 5, 7 and 8 suggests there is a low level of DNA contamination in the RNA sample, but shows that the majority of clusters in lane 6 are generated from RNA.

The clusters on the flowcell were then sequenced. Table 1 shows the results of sequencing.

TABLE 1

Sequencing Summary

| | Lane | Lane Yield | Clusters (raw) | Clusters (PF) | 1$^{st}$ Cycle Int (PF) | % intensity after 20 cycles (PF) | % PF Clusters | % Align (PF) | Alignment Score (PF) | % Error Rate (PF) |
|---|---|---|---|---|---|---|---|---|---|---|
| PhiX | 1 | 116 | 177455 +/− 11971 | 161186 +/− 10237 | 289 +/− 9 | 86.80 +/− 0.97 | 90388 +/− 1.64 | 98.28 +/− 0.22 | 166.43 +/− 0.00 | 0.04 +/− 0.00 |
| PhiX | 2 | 78 | 116338 +/− 3547 | 108649 +/− 3484 | 282 +/− 8 | 86.4 +/− 0.75 | 93.39 +/− 0.37 | 98.11 +/− 0.07 | 166.03 +/− 0.11 | 0.05 +/− 0.01 |
| PhiX + Tn | 3 | 40 | 63725 +/− 1557 | 55752 +/− 1477 | 289 +/− 4 | 87.78 +/− 1.13 | 87.49 +/− 0.34 | 58.26 +/− 0.25 | 96.55 + 0.39 | 0.28 +/− 0.00 |
| PhiX + Tn | 4 | 23 | 42441 +/− 1497 | 32075 +/− 1307 | 267 +/− 16 | 88.48 +/− 1.77 | 75.56 +/− 0.76 | 35.54 +/− 0.63 | 57.81 +/− 0.99 | 0.49 +/− 0.02 |
| RNA + Tn | 5 | 3 | 13608 +/− 731 | 4332 +/− 510 | 295 +/− 54 | 121.18 +/− 17.78 | 32.00 +/− 4.62 | 55.95 +/− 15.91 | 49.00 +/− 24.03 | 2.76 +/− 0.37 |
| RNA + Tn | 6 | 4 | 20916 +/− 1519 | 5701 +/− 1642 | 179 +/− 35 | 219.02 +/− 82.12 | 26.98 +/− 6.47 | 25.45 +/− 8.27 | 19.48 +/− 13.01 | 2.77 +/− 0.70 |
| RNA + Tn + RNAse | 7 | 1 | 22597 +/− 4274 | 1627 +/− 317 | 190 +/− 65 | 104.24 +/− 35.64 | 7.43 +/− 1.99 | 12.12 +/− 6.14 | 3.69 +/− 2.40 | 3.45 +/− 0.83 |
| RNA + Tn + RNAse | 8 | 1 | 45904 +/− 10022 | 1033 +/− 156 | 178 +/− 22 | 108.42 +/− 12.14 | 2.26 +/− 0.35 | 41.32 +/− 9.19 | 46.18 +/− 19.94 | 1.47 +/− 0.72 |

Lanes 1, 3, 5 and 7 were amplified with Phusion, not assumed to amplify RNA.
Lanes 2, 4, 6, and 8 were amplified with AMV-RT, which amplifies DNA and RNA.
Sequencing for non-transposed lanes 1 and 2 with SBS3 + T, for transposed lanes 3-8 with Nx R1 primer.
Matrix and phasing adjusted, lanes 5-8 aligned to GFP As expected, over 90% of clusters passed chastity filters for lane 1 and 2 and of these over 98% aligned to PhiX as expected (Table 1). Lanes 3 and 4 which contained tagmented DNA:DNA duplexes exhibited a 10-20% reduction in clusters passing filter, of which between 75-87% of clusters aligned to PhiX. Given that tagmentation can reduce the length of a template, in some cases to a length too short to align effectively, a reduction in cluster passing filters and aligning is not unexpected. The clusters in lanes 7 and 8 should not sequence well since there should not be any template present (with the exception of contaminating DNA templates or undigested RNA stumps). As expected very few clusters passed filters: less than 7% of clusters passed filters of which only 12% aligned for the PHUSION DNA Polymerase extended templates and 41% aligned for the AMV-RT extended templates. Where no RNase treatment was done, only DNase, and the RNA extended with Phusion 32% of clusters passed filters of which 56+−16% aligned (Lane 5, Table 1). This may be due to a combination of residual DNA templates and some extension of DNA opposite RNA by PHUSION DNA Polymerase. In contrast, approximately 50% more clusters were observed in lane 6, where DNase treated RNA template was extended with AMV-RT and of which a similar % passed filter (~27%) to lane 6 with 25% aligning.

Figure 7A:
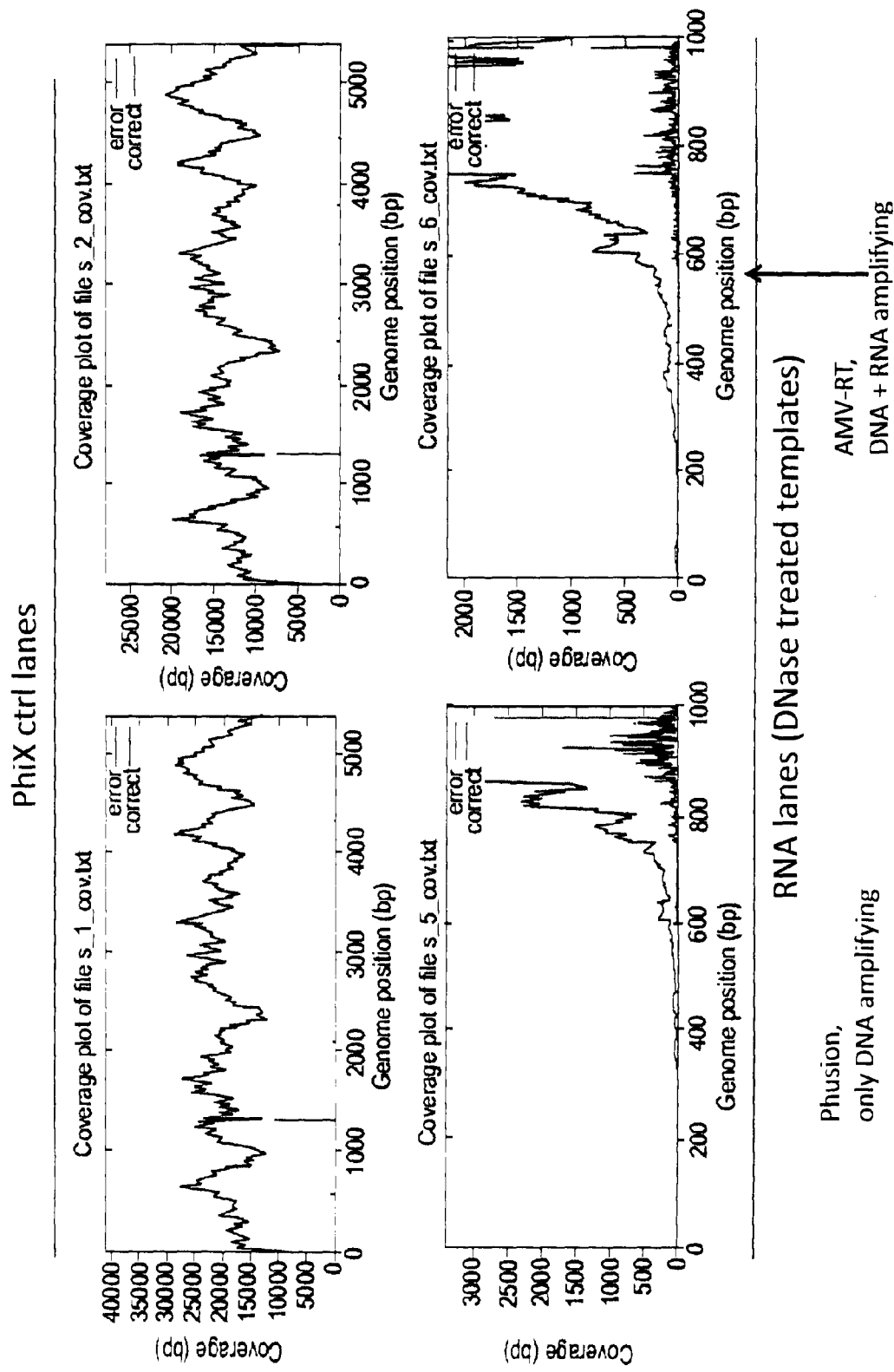
FIGS. 7A and 7B show graphs of coverage plots of the aligned sequencing data from sequencing of Lanes 1-8 as described for FIG. 6.
Figure 7B:
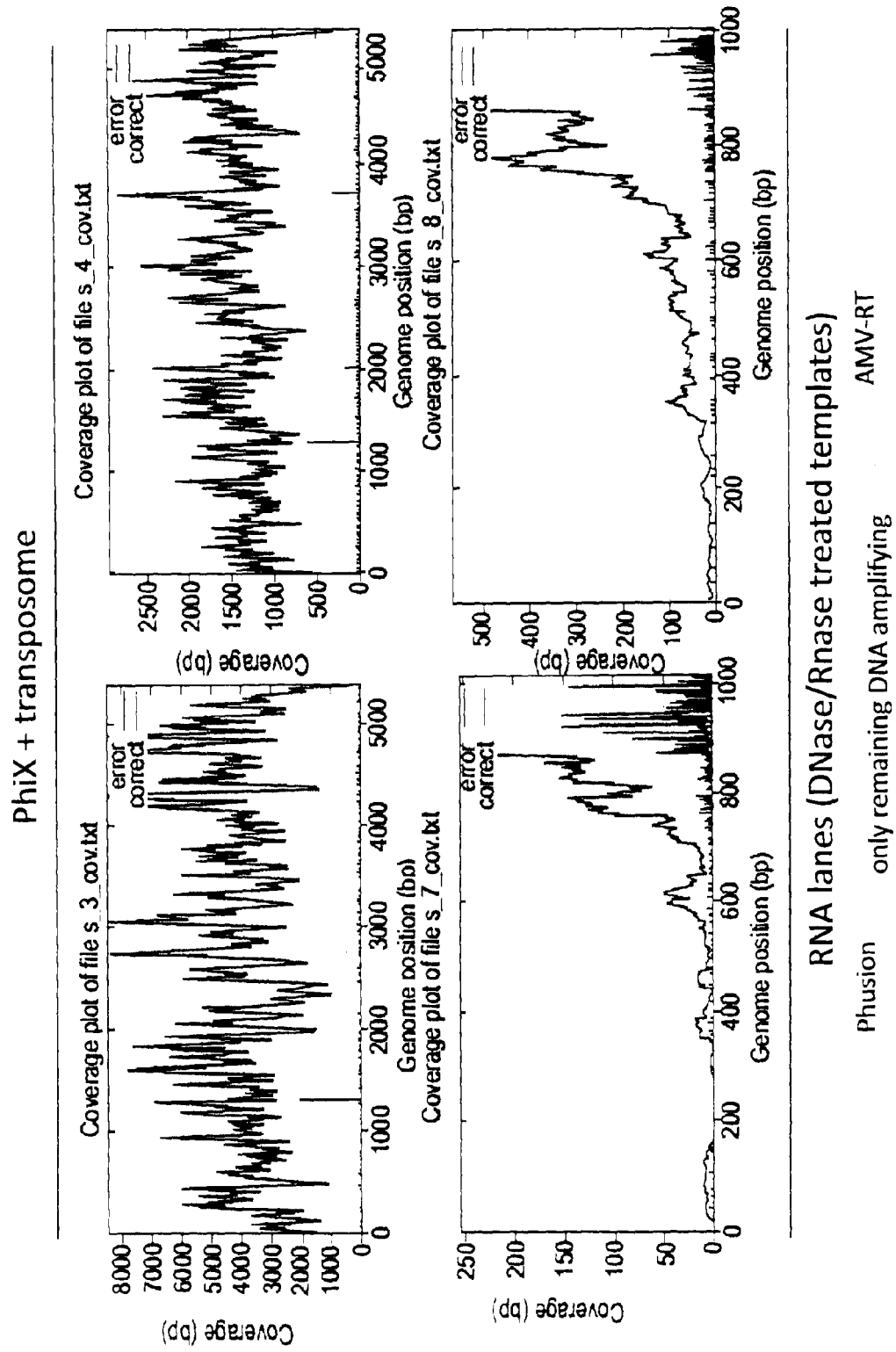

The aligned data was used to generate coverage plots (FIG. 7). Lanes 1-4 gave complete genome coverage of PhiX as expected. The lanes containing tagmented DNA (lanes 3 and 4) gave more uneven coverage. Lanes 5-8, containing tagmented RNA samples all showed partial coverage of the GFP, indicating that tagmentation of template has generated clusters. Given that some of this may derive from residual DNA template, lane 6 shows the widest coverage of the GFP template, indicating that AMV-RT extended RNA molecules have been tagmented successfully.

lanes 2-8 were grafted with standard mix (P5 and P7 oligos) plus the capture oligo (i.e., the primer comprising a polyT sequence for binding to RNA molecules comprising a polyA tail). After primer grafting, the flowcell was stored in 4° C. until it was used.

For lanes 1 and 2, 5 pM of PhiX control library samples were prepared and added to the flowcell for hybridization. For each lane 3-8, 400 ng of RNA sample was prepared and added to the flowcell for hybridization. Lanes 3 and 4 contained human RNA from Clontech (Mountain View, Calif.). Lanes 5 and 6 contained human RNA from brain. Lanes 7 and 8 contained universal human reference (UHR) RNA. After template hybridization, wash buffer was administered through the flowcell for removal of un-hybridized template. Hybridized templates were extended using AMV-RT (NEB, Ipswich, Mass.) in all lanes, which produced DNA:RNA duplexes in lanes 3-8.

While lanes 3-8 were contacted with a transposome complex, lanes 1 and 2 were contacted with equivalent volume of wash buffer. Transposome complex mixes of two different concentrations were prepared. The mix for lanes 3, 5 and 7 was prepared with 1.25 µl of transposome complex, 100 µl of buffer and 400 µl of water. The mix for lanes 4, 6 and 8 was prepared with 0.625 µl of transposome complex, 100 µl of buffer and 400 µl of water. 95 µl of transposome complex mixes were added to lanes 3-8 of the flowcell for tagmentation. To remove the transposase after tagmentation, chaotropic buffer was added to lanes 3-8 of the flowcell and incubated for 2 minutes. The lanes of the flowcell were then washed twice. After washing, Bst enzyme was used for strand displacement extension of tagmented DNA:RNA duplexes to remove the non-transferred strand of the transposon and make the DNA strand of the DNA:RNA duplexes full length for clustering. The RNA strands were removed and clusters were then generated using isothermal amplification. The clusters were then sequenced. Table 2 shows the results of sequencing.

TABLE 2

| | | | | | | | | |
|---|---|---|---|---|---|---|---|---|
| Sequencing Summary | | | | | | | | |
| Lane | Sample | Clusters (raw) | Clusters (PF) | 1$^{st}$ Cycle Int (PF) | % int after 20 cyc (PF) | % PF Clusters | % Align (PF) | % Error Rate (PF) |
| 1 | PhiX DNA 2 primer | 73569 +/− 8007 | 68422 +/− 7981 | 284 +/− 13 | 87.51 +/− 2.89 | 92.94 +/− 0.77 | 97.99 +/− 0.23 | 0.06 +/− 0.00 |
| 2 | PhiX DNA 3 primer | 18553 +/− 2932 | 11200 +/− 2451 | 206 +/− 10 | 99.83 +/− 6.39 | 60.00 +/− 4.34 | 1.55 +/− 1.36 | 8.78 +/− 1.60 |
| 3 | Clontech 1x Tn5 | 187046 +/− 29545 | 164971 +/− 26054 | 209 +/− 13 | 85.35 +/− 2.94 | 88.23 +/− 1.30 | 73.27 +/− 0.46 | 0.30 +/− 0.00 |
| 4 | Clontech 0.5x Tn5 | 109889 +/− 13109 | 99558 +/− 13108 | 211 +/− 10 | 87.58 +/− 4.32 | 90.49 +/− 1.19 | 73.91 +/− 0.56 | 0.27 +/− 0.02 |
| 5 | Brain 1x Tn5 | 226164 +/− 31941 | 198031 +/− 28192 | 218 +/− 6 | 84.55 +/− 2.36 | 87.55 +/− 0.97 | 75.27 +/− 0.36 | 0.36 +/− 0.20 |
| 6 | Brain 0.5x Tn5 | 125939 +/− 21818 | 113273 +/− 18279 | 212 +/− 12 | 86.85 +/− 3.09 | 90.06 +/− 1.20 | 75.91 +/− 0.13 | 0.24 +/− 0.00 |
| 7 | UHR 1x Tn5 | 310276 +/− 21976 | 269047 +/− 17778 | 195 +/− 7 | 86.77 +/− 2.14 | 86.75 +/− 1.68 | 67.70 +/− 0.38 | 0.27 +/− 0.04 |
| 8 | UHR 0.5x Tn5 | 195323 +/− 16530 | 172838 +/− 15327 | 211 +/− 16 | 86.70 +/− 1.77 | 86.47 +/− 0.67 | 68.14 +/− 0.52 | 0.36 +/− 0.30 |

Example 2

RNA Sequencing Employing a Tagmentation Reaction of Human Samples

A flowcell with eight lanes was prepared comprising primers capable of hybridizing to RNA molecules comprising a polyA tail as follows. Lane 1 was grafted with a standard oligo mix only comprising P5 and P7 oligos and The sequencing results were compared to results obtained for standard RNA sequencing of human brain RNA and universal human reference RNA, which was carried out according to standard Illumina sequencing methods using standard Illumina sequencing reagents. Such methods are described in TRUSEQ RNA Sample Preparation Guide and HISEQ 2000 User Guide. The guides and reagents are available from Illumina, Inc. (San Diego, Calif.). The results are shown in Table 3.

TABLE 3

Comparison of Tagmentation Method with Standard RNA Sequencing Method

| | Clontech RNA | | | UHR RNA | | | Brain RNA | | |
|---|---|---|---|---|---|---|---|---|---|
| | Read1 | | Read2 | Read1 | | Read2 | Read1 | | Read2 |
| Total Clusters | 16,000,000 | | | 16,000,000 | | | 16,000,000 | | |
| PFClusters | 14,113,235 | 100% | 100% | 14,008,505 | 100% | 100% | 13,957,990 | 100% | 100% |
| usableClusters | 9,005,973 | 63.8% | 62.6% | 8,756,482 | 62.5% | 60.9% | 8,956,350 | 64.2% | 61.1% |
| noMatch | 622,294 | 4.4% | 2.2% | 600,138 | 4.3% | 2.7% | 484,158 | 3.5% | 3.1 |
| repeatMasked | 4,484,041 | 31.8% | 35.1% | 4,651,421 | 33.2% | 36.4% | 4,517,061 | 32.4% | 35.7% |
| spliceUsable | 9,058 | 0.1% | 4.9% | 6,427 | 0% | 3.3% | 22,719 | 0.2% | 7.0% |
| genomeUsable | 8,996,915 | 63.7% | 57.8% | 8,750,055 | 62.5% | 57.6% | 8,933,631 | 64% | 54.1% |
| chrM.fa | 2,045,187 | 14.5% | 14.1% | 2,570,314 | 18.3% | 17.9% | 737,706 | 5.3% | 5.3% |
| humRibosomal.fa | 9,409 | 0.1% | 0.1% | 7,248 | 0.1% | 0.1% | 8,839 | 0.1% | 0.1% |

| | Standard RNA Sequencing | | | |
|---|---|---|---|---|
| | UHR | UHR | Brain | Brain |
| Total Clusters | | | | |
| PFClusters | 78,895,928 | 100% | 80,670,795 | 100% |
| usableClusters | 59,010,700 | 74.8% | 59,821,123 | 74.2% |
| noMatch | 1,352,439 | 1.7% | 1,503,346 | 1.9% |
| repeatMasked | 18,525,758 | 23.5% | 19,342,556 | 24% |
| spliceUsable | 9,357,715 | 11.9% | 6,959,693 | 8.6% |
| genomeUsable | 49,652,985 | 62.9% | 52,861,430 | 65.5% |
| chrM.fa | 5,710,330 | 7.2% | 10,414,460 | 12.9% |
| humRibosomal.fa | 1,789,882 | 2.3% | 2,349,250 | 2.9% |

The results show normal alignment distribution for the RNA samples sequenced using the tagmentation method provided herein. The results show higher repeat masked clusters likely due to higher numbers of polyA sequences and more repeats in the 3' UTR regions of the RNA samples analyzed by the tagmentation method. The usable reads were about 10% lower than for the standard RNA sequencing protocol again likely due to more repeats in the RNA that was analyzed. The amount of ribosomal RNA is low as would be expected since mRNA was isolated and sequenced in the tagmentation method provided herein. The mitochondrial RNA is within normal limits.

Example 3

RNA Sequencing Employing a Tagmentation Reaction and a Cell Lysate

This example demonstrates that nucleic acid templates can be captured, tagmented and sequenced on a solid support using a crude cell lysate. Briefly, mouse cells were lysed using a Triton-X and Proteinase K solution. The lysate was applied to a flowcell, mRNA was captured and tagmented, and clusters were created and sequenced. As a control and for comparison, Universal Human Reference total RNA (UHR) was also captured, tagmented, clustered and sequenced. Table 4 synopsis the results of duplicate reads for each sample type.

TABLE 4

Sequencing data comparison between UHR and lysate mRNA

| | UHR | | mouse cell lysate | |
|---|---|---|---|---|
| | R1 | R2 | R1 | R2 |
| total reads | 4,726,081 | | 1,905,434 | |
| % PF | 86.89% | 84.59% | 83.94% | 84.79% |

TABLE 4-continued

Sequencing data comparison between UHR and lysate mRNA

| | UHR | | mouse cell lysate | |
|---|---|---|---|---|
| | R1 | R2 | R1 | R2 |
| aligned (of % PF reads) | 61.14% | 73.97% | 49.17% | 68.16% |
| unaligned (of % PF reads) | 28.42% | 12.00% | 34.01% | 8.45% |
| abundant (of % PF reads) | 10.44% | 14.03% | 16.82% | 23.39% |
| spliced alignments (% of aligned bases) | 0.80% | 11.14% | 0.62% | 10.73% |
| spliced alignments (of % PF reads) | 0.4893 | 8.2435 | 0.3054 | 7.3138 |
| human Ribosomal | 0.21% | 0.04% | 3.98% | 4.88% |
| human 5Sr | 0.01% | 0.01% | 0.02% | 0.17% |
| median insert | 135 | | 129 | |
| SD insert | 67.99 | | 66.97 | |
| duplicates | 41.66% | | 45.54% | |

Table 4 demonstrates that sequence was obtained directly from mRNA captured from a crude mouse cell lysate. The percentage of aligned reads dropped only about 10% when mRNA was captured directly from crude cell lysates compared to the UHR RNA sample (aligned of % PF reads). Further sequencing data comparing the UHR control with mouse lysate derived mRNA reported that the correct strand was captured and aligned at >97% for both the UHR and the mRNA from the mouse lysate. Further, coverage was comparable between the UHR control and the mRNA from lysate; roughly 65% untranslated region (UTR), roughly 16% coding region, roughly 13% intergenic region, and small percentage intronic reads. As such, the present methods can be used to capture, tagment, cluster and sequence mRNA from crude lysates.

Example 4

RNA Sequencing Employing a Tagmentation Reaction from Whole mRNA Transcript

This experiment was performed to demonstrate that a mRNA sample representing a whole transcript could be captured and tagmented on a solid support to provide sequence information following methods disclosed herein. Briefly, polyA RNA enrichment was performed from 50 ug of UHR total RNA (Agilent) using the PolyA Purist Kit (Ambion). RNA fragmentation of the enriched polyA mRNA was done in 25 ul of 1× T4 PNK Buffer (Epicentre) with 100 ng of polyA RNA, wherein the sample was heated to 95° C. for 5 min and chilled on ice. The fragmented RNA was phosphorylated with T4 PNK and the fragments were polyA tailed using 4 units of *E. coli* PolyA polymerase in 50 ul of 2× PolyA polymerase buffer containing 2 mM ATP (Epicentre). The polyadenylated fragmented mRNA was purified using the RNA Clean and Concentration kit (Zymo Research). Controls included a PhiX control to validate the sequencing chemistry performance and a non-total mRNA derived polyadenylated sample that was captured and tagmented to compare with the mRNA whole transcript captured from the complex total RNA UHR pool.

Sequencing data from replicate 1 (R1) of 2 is reported in Table 5 for the PhiX control (ctrl) control mRNA sample (3' capture) and mRNA derived from the total RNA sample (whole transcript).

script coverage of the mRNA derived from complex total RNA was approximately 43% UTR, 37% coding and relatively similar for intergenic and intronic regions. FIG. 10 demonstrates aligned transcript coverage for a representative gene, GAPDH; the control mRNA (3' capture) shows coverage mainly in the 3' region of the gene as expected, whereas coverage from the total RNA derived mRNA (whole transcript) shows more complete coverage of both the exonic and the UTR regions. As such, while the control mRNA sequences aligned to those regions associated with the 3' end of a transcript (the polyA tail region), the coverage from the mRNA derived from the total RNA demonstrated more complete, whole transcript reads, thereby demonstrating the utility of the methods for obtaining whole transcript information from a sample.

An alternative workflow was also performed to enrich the mRNA from a UHR total RNA sample for whole transcript sequencing. Double stranded cDNA was prepared from 500 ng of UHR total RNA and 50 ng random DNA hexamers. Excess primers were degraded by adding 20 units of Exonuclease I (Epicentre), incubating at 37° C. for 30 min followed by enzyme heat inactivation. RNA was removed by an enzyme mix of 1 U RNase I/10 U Hybridase (RNAse H, Epicentre) at 55° C. for 10 min. The reaction was purified using equal volumes of AMPure beads (Agencourt) and DNA was eluted in a 10 mM Tris HCl (pH8.0) buffer. The cDNA was polyA tailed using 20 U Terminal Transferase (New England Biolabs), 1 mM ATP and 1× Transferase buffer, incubating 37° C. for 10 min. followed by heat inactivation. For some of the samples, a 1:10 dilution of the random DNA hexamers was utilized. Further, for some of the samples the Exonuclease I step was omitted. The samples were then applied to a flowcell, captured, tagmented, clustered and sequenced. Controls included PhiX

TABLE 5

Replicate sequence summary for whole mRNA transcript

| R1 | Sample Yield (Mb) | Clusters (raw) | Clusters (PF) | 1st Cycle Int (PF) | % intensity after 20 cycles (PF) | % PF Clusters | % Align (PF) | Alignment Score (PF) | % Mismatch Rate (PF) | % >= Q30 bases (PF) | Mean Quality SCore (PF) |
|---|---|---|---|---|---|---|---|---|---|---|---|
| ctrl | 317 | 7,079,810 | 6,343,692 | 268 | 86.78 | 89.6 | 97.89 | 251.82 | 0.15 | 98.35 | 39.12 |
| 3' capture | 1,077 | 28,753,789 | 21,543,617 | 290 | 85.17 | 74.92 | 57.15 | 75.08 | 0.74 | 92.34 | 36.58 |
| whole transcript | 752 | 19,474,750 | 15,040,807 | 323 | 83.03 | 77.23 | 49.85 | 70.27 | 1.63 | 91.89 | 36.51 |

Table 5 reports that the percentage of aligned reads was comparable regardless of the mRNA source (% align (PF)) with high cluster generation. Additionally, sequence data showed that transcript coverage of the control mRNA (3' capture) was approximately 70% UTR, 19% coding region followed by intergenic and intronic region coverage. Trancontrol (ctrl), non tailed cDNA (non tailed ctrl), a dsDNA negative control, and a purified mRNA sample that followed the same method as described above, except using random RNA hexamers and omitting the Exonuclease I step.

Table 6 summarizes the first of two replicate sequencing runs.

TABLE 6

Replicate sequence summary for alternative whole mRNA transcript

| R1 | Yield (Mb) | Clusters (raw) | Clusters (PF) | 1st Cycle Int (PF) | % intensity after 20 cycles (PF) | % PF Clusters | % Align (PF) | Alignment Score (PF) | % Mismatch Rate (PF) | % >= Q30 bases (PF) | Mean Quality SCore (PF) |
|---|---|---|---|---|---|---|---|---|---|---|---|
| Lane 1-PhiX ctrl | 227 | 7,040,939 | 6,480,317 | 317 | 89.58 | 92.04 | 98.16 | 165.52 | 0.08 | 98.25 | 38.88 |
| Lane 2-No tail ctrl | 3 | 773,384 | 76,281 | 246 | 84.82 | 9.86 | 0.15 | 0.05 | 5.04 | 42.11 | 20.13 |
| Lane 3-RNAse, AMP, tail | 62 | 3,504,536 | 1,783,482 | 420 | 75.32 | 50.89 | 20.14 | 13.65 | 1.29 | 85.96 | 34.57 |
| Lane 4-1:10 | 15 | 1,353,520 | 429,352 | 339 | 91.53 | 31.72 | 8.37 | 6.38 | 1 | 62.02 | 27.88 |
| Lane 5-Exo, RNAse, AMP, tail | 97 | 4,922,187 | 2,774,812 | 373 | 83.4 | 56.37 | 40.74 | 27.62 | 1.47 | 86.68 | 34.8 |
| Lane 6-1:10 | 7 | 844,731 | 198,052 | 317 | 79.07 | 23.45 | 13.09 | 6.81 | 1.38 | 42.76 | 21.15 |
| Lane7-RNA primers | 29 | 2,164,633 | 840,373 | 377 | 92.34 | 38.82 | 17.28 | 13.89 | 0.7 | 79.14 | 32.88 |
| Lane 8-ds cDNA | 8 | 852,450 | 219,356 | 311 | 97.61 | 25.73 | 1.3 | 0.32 | 2.61 | 48.15 | 23.6 |

Table 6 demonstrates that the method of preparation of treating a sample with nucleases, Exo I and RNases H and I, following by bead purification and polyA tailing (Exo, RNAse, AMP, tail) can be used to provide a whole mRNA transcript sample for sequencing. FIG. 9 shows pictures of clustering on the flowcell with respect to the different conditions identified in Table 6. Lanes 1-8 in Table 1 correspond to the Lanes 1-8 in FIG. 9. The PhiX positive control shows a large number of clusters which corresponds to the highest yield and cluster count in the sequencing data. The negative control lanes 2 and 8, which show low number of clusters also correspond to two of three the lowest yield and cluster counts in the sequencing data. Diluting the random DNA hexamer primers 1:10, regardless of exonuclease digestion in the preparation method, was not optimal for sequencing, showing low cluster count in Table 6 supported by fewer clusters seen on FIG. 9. The method using RNAse H and I with Exonuclease I during sample preparation of whole mRNA transcripts resulted in the greatest numbers of clusters generated as well as % alignment after the PhiX positive control, followed by the preparation method where Exonuclease I digestion was not practiced. Further, the percentage of aligned reads (% align (PF)) are highest for Lane 5 and Lane 3, respectively, among the test Lanes. The results demonstrate that the alternative method described in this example for generating cDNA can be used to provide whole mRNA transcript information by sequencing using the capture and tagmentation methods described in this application.

Additional options for sample preparation include, but are not limited to, utilizing the disclosed methods for sequencing RNA from species that do not have polyadenylated RNA, such as bacterial mRNA. In this case, ribosomal RNA could first be removed and the remaining mRNA could be fragmented and polyA tailed as previously described. The mRNA could then be captured, tagmented, cluster amplified and sequenced as described above.

These results show that a variety of different types of RNA samples and DNA samples derived from RNA samples can be sequenced using the methods provided herein and that the methods provided herein provide approximately equivalent sequence results to current standard RNA sequencing protocols.

What is claimed is:

1. A method of tagging nucleic acid duplexes comprising the steps of:
   (a) providing a transposase and a transposon composition;
   (b) providing one or more nucleic acid duplexes immobilized on a support, wherein the one or more nucleic acid duplexes are DNA:RNA duplexes; and
   (c) contacting the transposase and transposon composition with the one or more nucleic acid duplexes under conditions wherein the one or more DNA:RNA duplexes and transposon composition undergo a transposition reaction to produce one or more tagged DNA:RNA duplexes, wherein the DNA:RNA duplexes are tagged on the 5' end of the RNA strand, and wherein the transposon composition comprises a double stranded nucleic acid molecule comprising a transferred strand and a non-transferred strand.

2. The method of claim 1, wherein the support comprises a plurality of immobilized primers.

3. The method of claim 2, wherein an RNA strand of the one or more nucleic acid duplexes comprises a sequence complementary to at least a portion of one or more of the immobilized primers.

4. The method of claim 3, wherein the DNA:RNA duplexes are provided by hybridizing one or more RNA molecules to the immobilized primers on the support and extending the primers hybridized to the RNA molecules using the RNA molecules as templates to produce the one or more DNA:RNA duplexes.

5. The method of claim 3, wherein the immobilized primers comprise a polyT sequence.

6. The method of claim 2, wherein the plurality of immobilized primers comprises a first subset of primers of a first sequence and a second subset of primers of a second sequence.

7. The method of claim 6, wherein the first subset of primers comprises a polyT sequence.

8. The method of claim 4, wherein the plurality of immobilized primers comprise target specific primers capable of hybridizing to the one or more RNA molecules.

9. The method of claim 4, wherein the one or more RNA molecules each comprise a 3' adaptor comprising a sequence complementary to the plurality of immobilized primers or a subset thereof; and wherein the hybridizing comprises hybridizing the one or more RNA molecules comprising the 3' adaptor to the immobilized primers.

10. The method of claim 1, wherein the transposition reaction results in the 5' tagged RNA strand comprising the transferred strand of the transposon composition and a gap between the 3' end of a complementary DNA strand and the non-transferred strand of the transposon composition.

11. The method of claim 10, further comprising contacting the one or more tagged DNA:RNA duplexes with a nucleic acid modifying enzyme under conditions to extend the 3' end of DNA strands to copy RNA strands to their 5' end.

12. The method of claim 11, wherein the nucleic acid modifying enzyme displaces the non-transferred strand of the transposon composition.

13. The method of claim 11, further comprising removing the RNA strands from the DNA:RNA duplexes to yield remaining DNA strands.

14. The method of claim 13, further comprising sequencing at least a portion of the remaining DNA strands.

15. The method of claim 13, further comprising copying at least a portion of the DNA strands to produce a second DNA strand complementary to the DNA strand of the DNA:RNA duplexes.

16. The method of claim 15, further comprising sequencing the second complementary DNA strand.

17. The method of claim 16, wherein the DNA strand of the DNA:RNA duplexes is removed prior to sequencing the second complementary DNA strand.

18. The method of claim 13, further comprising amplifying the remaining DNA strands to produce a plurality of double stranded DNA molecules comprising first and second amplified strands.

19. The method of claim 18, further comprising removing the first amplified strands.

20. The method of claim 19, further comprising sequencing at least a portion of the second amplified strands.

21. The method of claim 20, further comprising copying at least a portion of the second amplified strands to regenerate the first amplified strands.

22. The method of claim 21, further comprising removing the second amplified strands.

23. The method of claim 22, further comprising sequencing at least a portion of the first amplified strands.

24. The method of claim 1, wherein the support is selected from the group consisting of a bead, a plurality of beads, and planar support.

25. The method of claim 24, wherein a plurality of duplexes is provided, each duplex immobilized on a single bead.

26. The method of claim 18, wherein the amplification produces a cluster of amplicons.

27. The method of claim 1, wherein the transferred strand comprises a tag to preserve strand information.

28. A method of tagging nucleic acid duplexes comprising the steps of:
(a) providing a transposase and a transposon composition;
(b) providing one or more nucleic acid duplexes immobilized on a support, wherein the support comprises a plurality of immobilized primers comprising a first subset of primers comprising a polyT sequence and a second subset of primers comprising a second sequence; and
(c) contacting the transposase and transposon composition with the one or more nucleic acid duplexes under conditions wherein the one or more nucleic acid duplexes and transposon composition undergo a transposition reaction to produce one or more tagged nucleic acid duplexes, wherein the transposon composition comprises a double stranded nucleic acid molecule comprising a transferred strand and a non-transferred strand.

29. The method of claim 28, wherein the one or more nucleic acid duplexes are DNA:RNA duplexes and wherein the DNA:RNA duplexes are tagged on the 5' end of the RNA strand.

30. The method of claim 29, wherein the transposition reaction results in a 5' tagged RNA strand comprising the transferred strand of the transposon composition and a gap between the 3' end of a complementary DNA strand and the non-transferred strand of the transposon composition.

31. The method of claim 28, wherein the nucleic acid duplexes are DNA:DNA duplexes and wherein one of the strands of the DNA:DNA duplex is tagged at the 5' end of the DNA strand.

32. The method of claim 31, wherein the transposition reaction results in a 5' tagged DNA strand comprising the transferred strand of the transposon composition and a gap between the 3' end of a complementary DNA strand and the non-transferred strand of the transposon composition.

33. A method of tagging nucleic acid duplexes comprising the steps of:
(a) providing a transposase and a transposon composition;
(b) providing one or more nucleic acid duplexes immobilized on a support, wherein the support comprises a plurality of immobilized primers wherein the one or more nucleic acid duplexes comprises one or more DNA:RNA duplexes having an RNA strand or one or more DNA:DNA duplexes having a DNA strand, wherein the RNA strand or the DNA strand comprises a sequence complementary to at least a portion of one or more of the immobilized primers and wherein the immobilized primers comprise a polyT sequence; and
(c) contacting the transposase and transposon composition with the one or more nucleic acid duplexes under conditions wherein the one or more nucleic acid duplexes and transposon composition undergo a transposition reaction to produce one or more tagged nucleic acid duplexes, wherein the transposon composition comprises a double stranded nucleic acid molecule comprising a transferred strand and a non-transferred strand.

34. The method of claim 33, wherein the one or more nucleic acid duplexes are DNA:RNA duplexes and wherein the DNA:RNA duplexes are tagged on the 5' end of the RNA strand.

35. The method of claim 33, wherein the nucleic acid duplexes are DNA:DNA duplexes and wherein one of the strands of the DNA:DNA duplex is tagged at the 5' end of the DNA strand.

* * * * *

SEQUENCE LISTING

<160> NUMBER OF SEQ ID NOS: 3

<210> SEQ ID NO 1
<211> LENGTH: 19
<212> TYPE: DNA
<213> ORGANISM: artificial sequences
<220> FEATURE:
<221> NAME/KEY: source
<222> LOCATION: 1..19
<223> OTHER INFORMATION: /mol_type="DNA"
      /note="transferred transposon sequence "
      /organism="artificial sequences"

<400> SEQUENCE: 1
agatgtgtat aagagacag                                                19

```
<210> SEQ ID NO 2
<211> LENGTH: 19
<212> TYPE: DNA
<213> ORGANISM: artificial sequences
<220> FEATURE:
<221> NAME/KEY: source
<222> LOCATION: 1..19
<223> OTHER INFORMATION: /mol_type="DNA"
      /note="non-transferred transposon sequence "
      /organism="artificial sequences"

<400> SEQUENCE: 2
ctgtctctta tacacatct                                                  19

<210> SEQ ID NO 3
<211> LENGTH: 1003
<212> TYPE: DNA
<213> ORGANISM: artificial sequences
<220> FEATURE:
<221> NAME/KEY: source
<222> LOCATION: 1..1003
<223> OTHER INFORMATION: /mol_type="DNA"
      /note="GFP expression cassette"
      /organism="artificial sequences"

<400> SEQUENCE: 3
aatgatacgg cgaccaccga gatctacact ctttccctac acgacgctct tccgatctta    60
atacgactca ctataggcaa ttttaacttt actaaggaga attcaccatg aaacatcacc   120
atcaccacac gactacaaag acgatgacga caaggcgatc gtgagcaagg gcgaggagct   180
gttcaccggg gtggtgccca tcctggtcga gctggacggc gacgtaaacg ccacaagtt    240 cagcgtgtcc ggcggggcga gggcgatgcc acctacggca agctgaccct gaagttcatc   300
tgcaccaccg gcaagctgcc cgtgccctgg cccaccctcg tgaccaccct gacctacggc   360
gtgcagtgct tcagccgcta cccgaccaca tgaagcagca cgacttcttc aagtccgcca   420
tgcccgaagg ctacgtccag gagcgcacca tcttcttcaa ggacgacggc aactacaaga   480
cccgcgccga ggtgaagttc gagggcgaac cctggtgaac cgcatcgagc tgaagggcat   540
cgacttcaag gaggacggca acatcctggg gcacaagctg gagtacaact acaacagcca   600
caacgtctat atcatggccg acaagcagaa gaacgcatca aggtgaactt caagatccgc   660
cacaacatcg aggacggcag cgtgcagctc gccgaccact accagcagaa cacccccatc   720
ggcgacggcc ccgtgctgct gcccgacaac cactacctga gccccagtcc gccctgagca   780
aagaccccaa cgagaagcgc gatcacatgg tcctgctgga gttcgtgacc gccgccggga   840
tcactctcgg catggacgag ctgtacaagt aactgctgcc accgctgaga ataactagca   900
taaccccttg gggcctctaa acgggtcttg aggggttttt tgagatcgga agagcggttc   960
agcaggaatg ccgagaccga tctcgtatgc cgtcttctgc ttg                    1003
```